United States Patent [19]

Rainer

[11] 4,239,901
[45] Dec. 16, 1980

[54] PYRAZOL-1-YLPHENYLACETIC ACIDS

[75] Inventor: Georg Rainer, Constance, Fed. Rep. of Germany

[73] Assignee: Byk Gulden Lomberg Chemische Fabrik GmbH, Constance, Fed. Rep. of Germany

[21] Appl. No.: 841,382

[22] Filed: Oct. 12, 1977

[30] Foreign Application Priority Data

Oct. 14, 1976 [CH] Switzerland ............... 13138/76

[51] Int. Cl.³ .................. C07C 109/10; C07D 231/10
[52] U.S. Cl. ....................... 560/34; 562/430;
562/439; 562/456; 562/433; 562/452; 560/13;
260/501.2; 548/377; 548/378; 548/379;
424/273 P; 424/226; 564/149
[58] Field of Search ............. 260/518 R, 518 A, 519,
260/569, 558 H, 501.2, 465 G; 562/433, 439;
560/34

[56] References Cited

U.S. PATENT DOCUMENTS

| 2,858,314 | 10/1958 | Georgian | 260/518 R |
|---|---|---|---|
| 3,459,799 | 8/1969 | Gutmann et al. | 260/569 |
| 3,526,653 | 9/1970 | Shen et al. | 562/433 |
| 3,766,260 | 10/1973 | Carney et al. | 260/518 R |
| 3,867,452 | 2/1975 | Wilcox | 260/518 R |
| 3,957,850 | 5/1976 | Bouchara | 260/518 R |
| 4,026,896 | 5/1977 | Harita et al. | 260/518 R |

FOREIGN PATENT DOCUMENTS 1119334  7/1968  United Kingdom ............ 562/433

OTHER PUBLICATIONS

Winchester et al., J. Hetero. Chem., vol. 12 (3), pp. 547–549, (1975).
Bussey, Disertation Abst., vol. 36 (2)b, p. 715, (1975).
Kodama et al., Chem. Abst., vol. 88, p. 488, #74388w, (1978).
Kogyo Kogaku Zassi, #73 (2), pp. 348–351, (1970).

*Primary Examiner*—James H. Reamer
*Attorney, Agent, or Firm*—Berman, Aisenberg & Platt

[57] ABSTRACT

Pyrazol-1-ylphenylacetic acids of the formula

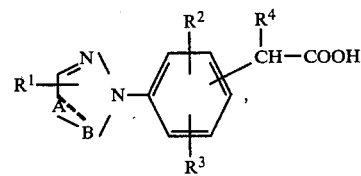

wherein
$R^1$, $R^2$ and $R^3$ are the same or different and denote a hydrogen atom or a halogen atom,
$R^4$ denotes a hydrogen atom or an alkyl group,
A=====B denotes a carbon-carbon single or double bond, and their salts are pharmacologically active and are useful as medicaments. Medicament compositions are produced therefrom. Their functional carboxylic acid derivatives and other new intermediates are used in their preparation.

13 Claims, No Drawings

PYRAZOL-1-YLPHENYLACETIC ACIDS

BACKGROUND

U.S. Pat. No. 3,896,143 concerns substituted pyrazol-3-ylphenylacetic acids and their derivatives, of which the 1,5-disubstituted pyrazol-3-ylphenylacetic acids are credited with having anti-inflammatory activity. Alkyl, optionally-substituted cycloalkyl and phenyl are regarded as suitable substituents on the pyrazole ring, while the phenylacetic acid radical is unsubstituted. In contrast to this, pyrazol-1-ylphenylacetic acids, unsubstituted or monosubstituted in the pyrazole radical, and their salts have an outstanding pharmacological effectiveness; they are also valuable intermediates for the preparation of pharmacologically-effective pyrazol-1-ylphenylacetic acids and their salts.

SUMMARY OF THE INVENTION

Pyrazol-1-ylphenylacetic acids (unsubstituted or monosubstituted on the pyrazole ring) and their salts are physiologically active. Those which are not pharmacologically acceptable are valuable intermediates in the preparation of their pharmacologically-acceptable counterparts. Those which are pharmacologically acceptable are useful as antiphlogistics, analgesics and antipyretics. They are administered orally or parenterally in virtually any standard medicament composition form in treating mammals afflicted with, e.g., inflammation, pain and/or fever.

The subject compounds are synthesized by known or analogy procedures from known starting materials or from starting materials which are readily prepared from available compounds.

DEFINITIONS

Throughout the specification a number of terms are used according to the following definitions unless otherwise stated.

alkyl—a monovalent, saturated, acyclic, straight-chain or branched hydrocarbon radical having from 1 to 6 carbon atoms. Except, possibly, with regard to valency, this definition applies as well to "alk" and "alkyl" of alkaryl, aralkyl, alkoxy, alkylamino, alkylmercapto, etc.

analgesic—relieving pain without causing loss of consciousness.

antiphlogistic—counteracting inflammation.

antipyretic—relieving or reducing fever.

aryl—a substituted or unsubstituted monovalent radical having up to 10 ring carbon atoms, including a single 6-membered aromatic carbocyclic ring, e.g., phenyl, or such a ring with a further ring condensed thereon, e.g. α-naphthyl and 2,3-dihydro-4-idenyl.

assymetric carbon—a carbon atom, conventionally designated by an asterisk (*), which has four different radicals or atoms attached to it.

carboxylic acid—R—COOH, wherein R is —H or an organic radical, a carbon atom of which is directly bound to the carbon atom of —COOH.

free hydrazino— —NH—NH$_2$.

functional carboxylic acid derivative— a —COOH derivative which is convertible into —COOH by lyolysis, preferably a nitrile, amide (e.g. —CO—NH$_2$) or ester (e.g. —CO—OCH$_3$). Illustrative functional carboxylic acid derivatives include nitrile (—CN), trichloromethyl (—CCl$_3$), trialkoxymethyl [e.g. —C(OCH$_3$)$_3$] and

wherein:

X is =O, =S or an optionally-substituted nitrogen atom, e.g. imino (=NH), alkylimino (e.g. =N—CH$_3$) and hydroxyimino (=N.OH); and Y is —OH or a monovalent cleavable electrophilic radical, in particular a free (—NH$_2$) or substituted amino group (e.g. benzylamino), preferably mono(lower)alkylamino (e.g. —NH—CH$_3$), di(lower)alkylamino [e.g. —N(CH$_3$)$_2$], arylamino (e.g. phenylamino), hydroxylamino (—NH—OH) or hydrazino (—NH—NH$_2$); free (—SH) or substituted mercapto group, preferably lower alkylmercapto (e.g. —SCH$_3$); substituted hydroxy, preferably alkoxy (e.g. —OCH$_3$), optionally-substituted benzyloxy (e.g. p-methylbenzyloxy) or phenoxy (e.g. p-chlorophenoxy); azido, chloro or bromo; Y is not hydroxy when X represents an oxygen atom.

halo or halogen—chloro (chlorine), fluoro (fluorine), bromo (bromine) or iodo (iodine), especially chloro, fluoro or bromo, particularly chloro or bromo and, preferably, chloro.

lower alkyl—alkyl or "alk" having from 1 to 5 carbon atoms, e.g. methyl, ethyl, propyl, isopropyl, butyl, tertiary butyl, secondary butyl and amyl. Of these ethyl is particularly noteworthy and methyl is preferred.

lyolyzed—split hydrolytically, hydrogenolytically or thermolytically.

protected hydrazine—a readily-splittable hydrazino-group derivative which, under reaction conditions, liberates the hydrazine group and thus reacts in the same manner as the hydrazino group. Such protected hydrazino groups are conventional and well known. They include, but are not limited to aromatic and aliphatic aldehyde hydrazones, e.g. benzaldehyde hydrazone

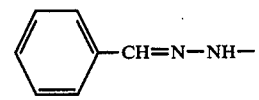

and acetaldehyde hydrazine CH$_3$—CH=N—NH—; aromatic and aliphatic ketone hydrazones, e.g. benzophenone hydrazone and acetone hydrazone; and acyl-substituted hydrazino, e.g. β-sulfohydrazino, α,β-disulfohydrazino and β-formylhydrazino.

substituted—bearing one or more substituents, generally at most three, advantageously not more than two and, preferably, only one; substitution is ordinarily at the favored position(s). Illustrative substituents of substituted aryl are, independently, halo, (e.g. in 3,5-dichlorophenyl), lower alkyl (e.g. in p-tolyl), lower alkoxy (e.g. in 2,4-dimethoxyphenyl), nitro (e.g. in o-nitrophenyl), amino (e.g. in p-aminophenyl), lower alkylamino (e.g. in p-ethylaminophenyl) and di(lower)alkylamino (e.g. in p-dimethylaminophenyl). Illustrative substituents for a substituted aliphatic carbon are, independently, halo, lower alkoxy, amino, lower alkylamino, di(lower)alkylamino, hydroxylamino, hydroxy (—OH), benzyloxy, phenoxy and phenyl. Illustrative substituents for substituted amino are, independently, lower alkyl, hydroxy, phenyl and benzyl.

salt—a compound of formula I wherein W is in the form of a salt of —COOH with an organic or inorganic base. Suitable cations include those of an alkalimetal, e.g. lithium, sodium and potassium; an alkaline-earth metal, e.g. calcium and magnesium; an earth metal, e.g. aluminum; ammonium; a mixture of two or more of the foregoing, e.g. a basic magnesium-aluminum complex salt; or copper; as well as the corresponding cation acids of monoacidic or polyacidic organic nitrogen bases, particularly of organic amines, such as the cation acids of ethanolamine, diethanolamine, triethanolamine, ethylenediamine, dimethylamine, diethylamine, morpholine, piperazine, methylcyclohexylamine, glucosamine, N-methylglycamine, N-methylglucosamine, tert.-butylamine, dibutylamine, diisopropylamine, triethylamine, isopropylamine, 2-amino-2-thiazoline, quinoline or amino acids, e.g. alanine, lysine, arginine and asparagine. The pharmacologically-acceptable, i.e. biologically-compatible, salts are preferred.

DETAILS

The invention has three aspects: compounds, medicament compositions and methods of use. The compounds are of the formula:

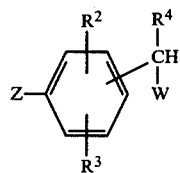

wherein
$Z$ is $R^1$-pyrazol-1-yl, $R^1$-pyrazolin-1-yl, free hydrazino or protected hydrazino;
each of
$R^1$, $R^2$ and $R^3$ is, independently, —H or halo;
$R^4$ is —H or lower alkyl; and
W is —COOH, a salt of —COOH with a base, or a functional —COOH derivative which is convertible into —COOH by lyolysis, i.e. hydrolysis, thermolysis or hydrogenolysis.

The most important compounds are those which are physiologically active and pharmacologically acceptable. Such compounds within the scope of this invention are those wherein Z is $R^1$-pyrazolin-1-yl and preferably $R^1$-pyrazol-1-yl. All compounds of formula I are intermediates in the preparation of one or more of the noted physiologically-active and pharmaceutically-acceptable compounds.

The medicament compositions are conventional in form, in make-up and in mode of preparation, except for the active component therein. The form, make-up and mode of preparation are conventional for enteral or parenteral administration to, e.g., a mammal afflicted with inflammation, pain and/or fever. The active compound is a physiologically-active and pharmacologically-acceptable compound of formula I wherein Z is $R^1$-pyrazol-1-yl or $R^1$-pyrazolin-1-yl. The amount or concentration of active component in such medicament compositions is that which is effective as an anti-inflammatory, as a pain reducer and/or as a fever reducer when administered to a subject afflicted with one or more of these conditions.

The physiologically-active and pharmacologically-acceptable compounds and the medicament compositions in which they are incorporated are useful as antiphlogistics, analgesics and antipyretics, i.e. as anti-inflammatories, as pain reducers and as fever reducers.

The compounds of formula I are subsequently referred to in distinct and more restricted categories which are identified as follows:
(A) a compound of formula I wherein Z is $R^1$-pyrazol-1-yl or $R^1$-2-pyrazolin-1-yl, and W is —COOH;
(B) a compound (A) wherein Z is 4-$R^1$-pyrazol-1-yl;
(C) a compound (B) wherein at least one of $R^1$, $R^2$ and $R^3$ is halo, and Z is para to

(D) a compound (C) wherein $R^2$ is ortho to Z, at least one of of $R^1$ and $R^2$ is halo, $R^3$ is —H, and $R^4$ is —H, —CH$_3$ or —CH$_2$CH$_3$;
(E) a compound of formula I wherein W is —COOH, and Z is hydrazino or protected hydrazino, i.e. other than p-hydrazinophenylacetic acid;
(F) a compound (E) wherein $R^3$ is —H, and

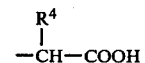

is meta to $R^2$ and para to Z; and
(G) a compound (F) wherein $R^2$ is halo, and $R^4$ is —H or —CH$_3$.

Illustrative of compounds IA are those of the formula

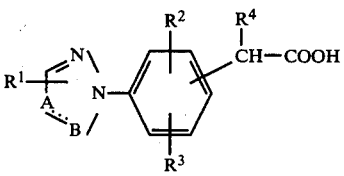

wherein each of
$R^1$, $R^2$ and $R^3$ is, independently, a hydrogen atom (—H) or halo;
$R^4$ is a hydrogen atom (—H) or alkyl (preferably lower alkyl); and
A⋯⋯B denotes two carbon atoms bound together by either a single or a double bond.

These compounds IA are closely associated with and are regarded as the same aspect of the invention as their salts with organic or inorganic bases and their functional carboxylic-acid derivatives.

As the invention encompasses asymmetric-carbon-containing compounds, it includes enantiomers, their mixtures and racemates of such compounds.

A particular embodiment of the invention encompasses those pyrazol-1-ylphenylacetic acids of formula II wherein each of
$R^1$, $R^2$ and $R^3$ is, independently a hydrogen atom (—H), fluoro or, preferably, bromo or chloro;
$R^4$ is a hydrogen atom (—H) or alkyl having from 1 to 5 carbon atoms, e.g. amyl, butyl, propyl, ethyl and methyl (of which ethyl and, more particularly, methyl are preferred); and A ⸺ B denotes two carbon atoms bound together by a double bond;

their salts (with inorganic or organic bases) and their functional carboxylic-acid derivatives. Of these, compounds IB (wherein Z is 4-$R^1$-pyrazol-1-yl), their salts with inorganic or organic bases and their functional carboxylic acid derivatives are preferred.

For all embodiments of the invention these compounds having a free carboxyl group and the salts thereof are preferred over counterparts in the form of a functional carboxylic acid derivative.

Select compounds from those designated IB are compounds IC (particularly those wherein at least one of $R^1$, $R^2$ and $R^3$ is bromo or chloro) and their salts with inorganic or organic bases.

Especially noteworthy of compounds IC are those designated ID and their salts with inorganic or organic bases. Those compounds ID (and their salts with organic or inorganic bases) in which each of $R^1$ and $R^2$ is halo (the same or different and, preferably, bromo or chloro) and $R^4$ is —H or methyl are extraordinary and, of this last-noted group, those compounds wherein $R^2$ is chloro are preferred.

All pyrazol-1-ylphenylacetic acids of formula II are pharmacologically active and physiologically acceptable. Exemplary compounds IB of formula II are:

4-(pyrazol-1-yl)phenylacetic acid,
2-[4-(pyrazol-1-yl)phenyl]propionic acid,
4-(4-chloropyrazol-1-yl)phenylacetic acid,
4-(4-bromopyrazol-1-yl)phenylacetic acid,
2-[4-(4-chloropyrazol-1-yl)phenyl]propionic acid,
2-[4-(4-bromopyrazol-1-yl)phenyl]propionic acid,
3-chloro-4-[4-chloropyrazol-1-yl]phenylacetic acid,
3-chloro-4-[4-bromopyrazol-1-yl]phenylacetic acid,
2-[3-chloro-4-(4-bromopyrazol-1-yl)phenyl]propionic acid
2-[3-bromo-4-(4-chloropyrazol-1-yl)phenyl]propionic acid and particularly
2-[3-chloro-4-(4-chloropyrazol-1-yl)phenyl]propionic acid.

The salts (with inorganic and organic bases) of each of the preceding compounds are inseparable from and a part of the same aspect of this invention.

The compounds according to the invention and their salts exhibit distinct antiphlogistic, besides analgesic and antipyretic, properties, as can be evidenced, e.g., by various tests which confirm the influence of the compounds on acute inflammation reactions {carrageenin oedema of rat hind paw [Winter et al., *Proc. Soc. exp. Biol. Med.*, 111 (1962) 544]}, as well as chronic inflammation processes {cotton pellet test on the rat [Winter et al., *J. Pharmacol. exp. Therap.*, 141 (1963), 369] and adjuvant arthritis [on the basis of Perrine et al., Brit. J. Pharmacol. 21 (1963) 127]}. These compounds are superior to prior art compounds, e.g. those of U.S. Pat. No. 3,896,143 and the commercial medicament, phenylbutazone. In addition, they are distinguished by comparatively low toxicity.

By enteral or parenteral administration to an afflicted host of a therapeutically-effective and pharmacologically-compatible amount, the physiologically-acceptable compounds according to the invention are thus useful for treating a multiplicity of mammalian illnesses in which one or more symptoms of inflammation, pain and fever occur. Such illnesses include the most diverse inflammatory and degenerative diseases of rheumatic form and other inflammatory disease processes, e.g. acute and chronic polyarthritis, osteoarthritus, psoriatic arthritis, ankylosing spondlitus, polyarthroses, spondyloses, articular rheumatism, rheumatic fever; rheumatism of soft tissues, e.g. tendinitus, periarthritus and periostitis; acute muscular rheumatism, e.g. sciatica; painfully postoperative swellings and inflammations; pain and swelling after effusion of fluid into a joint; sprains and fractures; pain and inflammation in connection with dental surgery; pains of the most diverse origin, e.g. neuritides, headaches and spasms; as well as human and animal illnesses which result in the aforesaid symptoms and call for administration of anti-inflammatory, analgesic and/or antipyretic medicament.

One aspect of the invention is, therefore, a process for treating mammals which are ill and have one or more symptoms of inflammation, pain or fever. The process is characterized by administering a therapeutically-effective and pharmacologically-compatible amount of one or more physiologically-active and pharmacologically-acceptable compounds of formula I and/or its salts to such an afflicted mammal.

Another aspect of the invention comprises medicament characterized by a content of one or more of the new active substances. Where appropriate, the new medicament contains (in addition to the noted active substance) pharmaceutical excipient for such active substance. The active-substance content of these medicaments is from 1 to 95, preferably from 10 to 85, percent by weight, with reference to the finished medicament.

The medicaments are preferably administered orally; they are also applied rectally, topically (percutaneously) or, as solutions of salts, parenterally (e.g. injected subcutaneously, intramuscularly or intravenously). Advantageously, the pharmaceutical preparation of the active substance is in unit-dose form, which is matched to the desired mode of administration. A unit dose may be in the form of, e.g., a tablet, a capsule, a suppository or a measured volume amount of a powder, a granulate, a solution, an emulsion, a suspension, a gel or an ointment. By "unit dose" in the sense of the present invention is understood a physically-specified unit which contains an individual amount of active constituent in admixture with a pharmaceutical diluent therefor or together with a pharmaceutical excipient. The amount of the active substance is so chosen that one or more units are usually needed for an individual therapeutic administration. The unit dose may, however, also be subdivisible, e.g. in the case of tablets provided with grooves, when only a fraction, such as a half or a quarter, of the subdivisible unit is needed for a single therapeutic administration.

The pharmaceutical preparations according to the invention contain (when present in a unit dose for administration to humans) from 1 to 1,000 milligrams (mg), advantageously from about 5 to 500 mg and, in particular, from about 10 to about 250 mg, of active substance according to this invention. The unit doses for administration to mammals of smaller or greater weight are weight (of mammal) dependent; thus, for example, unit doses for large animals, such as cattle or horses, contain from 100 to 10,000 mg, advantageously from 200 to 6,000 mg and, in particular, from 300 to 4,000 mg, of active substance. Therapeutic administration of the pharmaceutical preparations are effected, e.g., from 1 to 4 times daily, e.g. after each meal and/or in the evening. The administered dose is governed by frequency of administration, duration of treatment, the nature and gravity of the illness and by the weight, the age and the state of health of the subject. In general, the daily dose for mammals lies between 0.05 and 70 mg per milogram (kg) of body weight, preferably below 30 mg/kg of body weight. An expedient daily dose for humans lies between 1 and 10 mg/kg of body weight.

The pharmaceutical preparations generally consist of active substances according to the invention and non-toxic, pharmaceutically-acceptable medicament excipients which are used as additive in solid, semi-solid or liquid form or as an encapsulating agent, for example in the form of a capsule, a tablet coating, a bag or other container for the therapeutically-active constituent. An excipient may serve, e.g., as vehicle for the uptake of the medicament by the body, as formulation auxiliary, as sweetener, as flavoring, as coloring matter or as preservative.

Tablets, dragees, hard and soft capsules, e.g. of gelatin, dispersible powders, granulates, aqueous and oily suspensions, emulsions, solutions or syrups are, e.g., used for oral administration. These dosage forms are conventional. They are made by conventional procedures from ingredients which (other than the subject active ingredients) are also entirely conventional.

Tablets optionally contain inert diluents, e.g. calcium carbonate, calcium phosphate, sodium phosphate or lactose; granulating and distributing agent, e.g. maize starch or alginate; binder, e.g. starch, gelatin or acacia gum; and glidant, e.g. aluminum stearate or magnesium stearate, talc or silicone oil. They are additionally optionally provided with a coating which may also be of such a nature that it causes delayed dissolution and resorption of the medicament in the gastro-intestinal tract and thus, e.g., better compatibility or an extended duration of action. Gelatin capsules optionally contain the medicament in admixture with solid diluent, e.g. calcium carbonate or kaolin, or an oily diluent, e.g. olive oil, arachis oil or paraffin oil.

Aqueous suspensions optionally contain suspending agent, e.g. sodium carboxymethylcellulose, methylcellulose, hydroxypropylcellulose, sodium alginate, polyvinylpyrrolidone, gum tragacanth or acacia gum; dispersing and wetting agents, e.g. polyoxyethylene stearate, heptadecaethyleneoxycetanol, polyoxyethylenesorbitol mono-oleate, polyoxyethylene sorbitan mono-oleate or lecithin; preservative, e.g. methyl or propyl hydroxybenzoate; flavoring; sweetener, e.g. sucrose, lactose, dextrose or invert sugar syrup. Oily suspensions optionally contain, e.g., arachis oil, olive oil, sesame oil, coconut oil or paraffin oil; thickener, e.g. beeswax, hard paraffin or cetyl alcohol; sweetener; flavoring; and anti-oxidant.

Powders and granulates which are dispersible in water optionally contain the medicament in admixture with dispersing, wetting and suspending agent, e.g. those previously mentioned, as well as with sweetener, flavoring and coloring matter.

Emulsions optionally contain, e.g. olive oil, arachis oil or paraffin oil, besides emulsifier, e.g. acacia gum, gum tragacanth, phosphatides, sorbitan mono-oleate or polyoxyethylenesorbitan mono-oleate; sweetener and flavoring. Suppositories are used for rectal administration of the medicament. These are prepared with the aid of binder, for example cocoa butter or a polyethyleneglycol, which melts at rectal temperature.

For parenteral administration of the medicament, a sterile injectable aqueous suspension, isotonic salt solution or other solution is used. Each optionally contains dispersing or wetting agent and/or pharmacologically-compatible diluent, e.g. propylene or butylene glycol.

Besides the new pyrazol-1-ylphenylacetic acids, the pharmaceutical preparations optionally contain one or more pharmacologically-active constituents from other medicament groups, for example an anti-inflammatory corticosteroid, e.g. prednisone, prednisolone, dexamethasone and their derivatives;

analgesic, for example a pyrazolone derivative (e.g. aminophenazone), propoxyphene, phenacetin, a salicylic acid derivative, etc.;

muscle relaxant, such as a pyridazine derivative, carbamate (e.g. phenprobamate), etc.;

substances with anti-ulcerogenic activity;

antacid, for example magnesium trisilicate and aluminum hydroxide;

substances which locally stimulate blood circulation, for example a nicotinic acid derivative and dimethyl sulfoxide; local anesthetic, for example lidocaine, and vitamin, for example vitamin $B_1$ chloride hydrochloride, vitamin $B_6$ hydrochloride, vitamin $B_{12}$ cyano complex and thiamine disulfide.

A process for preparing pyrazol-1-ylphenylacetic acids of formula II and of their salts with inorganic and organic bases is characterized by a functional carboxylic-acid derivative (of a pyrazol-1-ylphenylacetic acid of formula II) which is of formula III

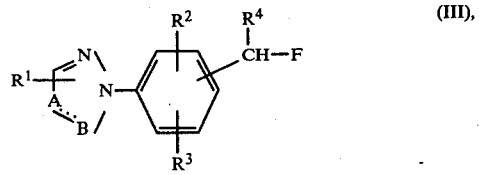

wherein
$R^1$, $R^2$, $R^3$, $R^4$ and A┄┄┄B have their previously-ascribed meanings and
F denotes a functional derivative of a carboxylic-acid group, and which is lyolyzed, i.e. split hydrolytically, hydrogenolytically or thermolytically, to yield a corresponding compound of formula II or a salt thereof; where appropriate, the obtained acid of the formula II or its salt is, in customary manner, subsequently dehydrogenated and/or halogenated and/or converted into another such compound. If desired, a compound of formula II (obtained in the form of a free acid) is converted into a corresponding salt, or a compound of formula II (obtained in the form of a salt) is converted into the corresponding free acid or into another salt.

Conversion from one salt to another, e.g. from a toxic to a pharmacologically-acceptable salt, from a salt to the corresponding free acid or from the free acid to a salt is entirely conventional and is effected by well-established procedures.

In a preferred embodiment of the process, a functional pyrazol-1-ylphenylacetic acid derivative of formula III
wherein
A┄┄┄B denotes two carbon atoms bound together by a double bond;
$R^1$ is in the 4-position;
$R^1$, $R^2$, $R^3$ and $R^4$ have their previously-stated meanings and F denotes nitrile (—CN), trichloromethyl (—CCl₃), trialkoxymethyl or the radical

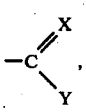

X represents an oxygen atom (=O), a sulfur atom (=S) or a substituted nitrogen atom, in particular imino (=NH), alkylimino or hydroxyimino, and Y denotes hydroxy (=OH) or a monovalent eliminable electrophilic radical, in particular a free or substituted amino group, preferably monoalkylamino, dialkylamino, arylamino, hydroxyamino or hydrazino; free or substituted mercapto, preferably alkylmercapto; substituted hydroxy, preferably alkoxy, optionally-substituted benzyloxy or phenoxy; azido, chloro or bromo; Y is not hydroxy when X represents an oxygen atom, is hydrolytically split.

Each alkyl of trialkoxymethyl, alkylimino, monoalkylamino, dialkylamino, alkylmercapto, alkoxy or phenalkoxy is, e.g., methyl, ethyl, isopropyl, n-butyl and pentyl, with up to 6 carbon atoms; aryl of arylamino is an aryl, e.g. phenyl, α-naphthyl and β-naphthyl, with up to 10 ring carbon atoms.

A further preferred embodiment comprises hydrolytically splitting a functional pyrazol-1-ylphenylacetic acid derivative of formula III, in which F is —CN or the group

X denotes an oxygen atom (=O), a sulfur atom (=S) or imino (=NH), and

Y denotes amino (—NH₂), monoalkylamino, dialkylamino, phenylamino, alkoxy, phenalkoxy, phenoxy, alkylthio, chloro or bromo.

Particularly preferred embodiments of the process comprise hydrolytically splitting pyrazol-1-ylphenylacetic acid nitriles, pyrazol-1-ylphenylacetic acid amides, chlorides, bromides or esters of formula III, wherein A⋯⋯⋯B comprises two carbon atoms bound together by a double bond.

The process is optionally carried out with a pyrazolylphenylacetic acid derivative which forms, as an intermediate, a pyrazolylphenylacetic acid derivative of formula III, which subsequently reacts with water-donating medium to yield the desired pyrazolylphenylacetic acid derivative of formula II. In many cases, the process proceeds in several steps and, with suitable reaction management, intermediate steps are optionally isolated. Thus, for example, the hydrolytic splitting of nitriles, thioamides, amidines and imidazolines proceeds via corresponding amides, or the hydrolytic splitting of carboximidic acid esters proceeds via carboxylic acid esters. The reaction of unsubstituted amides with nitrous acid produces acyldiazonium compounds, as intermediates, which readily hydrolyze to corresponding carboxylic acids. By treating an acetic acid halide with a tertiary amine, a ketene derivative is formed as an intermediate which react in the presence of or subsequently with water to give the pyrazolylphenylacetic acid of formula II.

As starting material for the process of the invention for the preparation of compounds of formula II, those compounds are suitable which, as functional derivatives of carboxylic acids of formula II, yield a compound of formula II through splitting (lyolysis). Such functional carboxylic acid derivatives (in the case of lyolysis with water) include alkyl esters (e.g. methyl ester or ethyl ester), phenyl esters (e.g. p-nitrophenyl ester), benzyl esters (e.g. p-methoxybenzyl ester), alkoxyalkyl esters (e.g. methoxymethyl ester), dialkylaminoalkyl esters, (e.g. β-dimethylaminoethyl ester), amides, N-monoalkylamides (e.g. N-methylcarboxamide), N,N-dialkylamides (e.g. N,N-dimethylcarboxamide), morpholides (e.g. morpholinocarbonyl), piperidides (e.g. piperidinocarbonyl), piperazides (e.g. piperazinocarbonyl), anilides, N-alkylanilides (e.g. N-methylanilinocarbonyl), N-hydroxylamides, N-alkoxyamides (e.g. N-methoxycarboxamide), hydrazides, azides, mono- and dithiocarboxylic acids, thiocarboxylic acid S- and O-alkyl esters (e.g. thiocarboxylic acid S- and O-ethyl ester), dithiocarboxylic acid alkyl esters (e.g. dithiocarboxylic acid methyl ester), thioamides, thiomorpholides, carboximidic acid esters (e.g. ethyl carboximidate), amidines, hydrazidines, oxazolines, imidazolines, thiazolines, acid chlorides, acid bromides, acid anhydrides, ketenes and nitriles.

Particularly important starting compounds, however, are those whose preparation is most feasible from an industrial and economic point of view and which are best described by formula III, wherein A⋯⋯⋯B represents two carbon atoms bound together by a double bond. When radicals X and Y are eliminated during hydrolytic splitting, their chemical structure is, naturally, of secondary importance. Some compounds, on account of possible tautomerism (e.g. carboxamide-carboximidic acid), are optionally represented by two different structural formulations.

For the aforesaid process of lyolysis with water, characteristic starting products include, for example, nitriles, amides and carboxylic acid lower alkyl esters of formula III, e.g.:

2-[3-chloro-4-(4-chloropyrazol-1-yl)phenyl]propionitrile
2-[3-chloro-4-(4-bromopyrazol-1-yl)phenyl]propionitrile
2-[3-chloro-4-(4-fluoropyrazol-1-yl)phenyl]propionitrile
2-[3-chloro-4-(pyrazol-1-yl)phenyl]propionitrile
2-[4-(4-chloropyrazol-1-yl)phenyl]propionitrile
2-[4-(4-bromopyrazol-1-yl)phenyl]propionitrile
2-[4-(4-fluoropyrazol-1-yl)phenyl]propionitrile
2-[4-(4-iodopyrazol-1-yl)phenyl]propionitrile
2-[4-(pyrazol-1-yl)phenyl]propionitrile
2-[3-bromo-4-(pyrazol-1-yl)phenyl]propionitrile
2-[3-bromo-4-(4-chloropyrazol-1-yl)phenyl]propionitrile
3-chloro-4-(4-chloropyrazol-1-yl)phenylacetonitrile
3-chloro-4-(4-bromopyrazol-1-yl)phenylacetonitrile
3-chloro-4-(pyrazol-1-yl)phenylacetonitrile
4-(4-chloropyrazol-1-yl)phenylacetonitrile
4-(4-bromopyrazol-1-yl)phenylacetonitrile
4-(pyrazol-1-yl)phenylacetonitrile
3-bromo-4-(pyrazol-1-yl)phenylacetonitrile
3-bromo-4-(4-chloropyrazol-1-yl)phenylacetonitrile
2-[3-chloro-4-(4-chloropyrazol-1-yl)phenyl]propionamide 2-[3-chloro-4-(4-chloropyrazol-1-yl)phenyl]-N,N-dimethylpropionamide
2-[3-chloro-4-(4-chloropyrazol-1-yl)-phenyl]-N-(n-butyl)propionamide
2-[3-chloro-4-(4-chloropyrazol-1-yl)phenyl]propionmorpholide
2-[3-chloro-4-(4-chloropyrazol-1-yl)phenyl]propionhydrazide
2-[3-chloro-4-(4-chloropyrazol-1-yl)phenyl]propionthiomorpholide
2-[3-chloro-4-(4-chloropyrazol-1-yl)phenyl]propionyl chloride
2-[3-chloro-4-(4-chloropyrazol-1-yl)phenyl]propionic acid methyl ester
2-[3-chloro-4-(4-chloropyrazol-1-yl)phenyl]propionic acid tert.-butyl ester
2-[3-chloro-4-(4-chloropyrazol-1-yl)phenyl]propionic acid benzyl ester
2-[3-chloro-4-(4-chloropyrazol-1-yl)phenyl]propionic acid phenyl ester
2-[3-chloro-4-(4-chloropyrazol-1-yl)phenyl]-N-methylpropionanilide
2-[3-chloro-4-(4-chloropyrazol-1-yl)phenyl]propionamidoxime
2-[3-chloro-4-(4-bromopyrazol-1-yl)phenyl]-N,N-dimethylpropionamide
3-chloro-4-(4-chloropyrazol-1-yl)phenyl-N,N-dimethylacetamide
2-[3-chloro-4-(4-fluoropyrazol-1-yl)phenyl]propionic acid ethyl ester
2-[3-chloro-4-(4-bromopyrazol-1-yl)phenyl]propionic acid ethyl ester
2-[3-chloro-4-(pyrazol-1-yl)phenyl]propionic acid ethyl ester
2-[4-(pyrazol-1-yl)phenyl]propionic acid ethyl ester
2-[3-bromo-4-(4-chloropyrazol-1-yl)phenyl]propionic acid ethyl ester
3-chloro-4-(4-chloropyrazol-1-yl)phenylacetic acid ethyl ester
3-bromo-4-(4-chloropyrazol-1-yl)phenylacetic acid ethyl ester
3-chloro-4-(4-fluoropyrazol-1-yl)phenylacetic acid ethyl ester
3-chloro-4-(4-bromopyrazol-1-yl)phenylacetic acid ethyl ester
3-chloro-4-(pyrazol-1-yl)phenylacetic acid ethyl ester
4-(4-chloropyrazol-1-yl)phenylacetic acid ethyl ester
2-[3-chloro-4-(4-chloropyrazol-1-yl)phenyl]butyric acid ethyl ester
2-[3-chloro-4-(pyrazol-1-yl)phenyl]butyric acid ethyl ester
3-chloro-4-(4-chloropyrazol-1-yl)phenylacetic acid phenyl ester
3-chloro-4-(4-chloropyrazol-1-yl)phenylacetic acid benzyl ester.

For the hydrolytic splitting of functional carboxylic acid derivatives of formula III, a water-donating medium is used. Such a medium consists wholly or partially of water or of agents which, under reaction conditions, split off water or $OH^{\ominus}$ ions. The reaction is, e.g., conducted as a homogeneous reaction in a polar organic solvent or in contact with a solubilizer. Advantageously-used solvents include, for example, low-molecular-weight alcohols (e.g. methanol or ethanol), dioxan, acetone, low-molecular-weight carboxylic acids (e.g. acetic acid and propionic acid), N-methylpyrrolidone, sulfolane or dimethylsulfoxide. The reaction is, alternatively, conducted as a heterogeneous reaction. The pH of the water-donating medium is governed by the chemical nature of the pyrazol-1-yl-phenylacetic acid derivative used and by the nature of the desired compound of formula II; it may, therefore, be neutral, acid or basic. It is adjusted to the desired value with acid, base or buffer. The reaction temperature is between 0° C. and the boiling point of the water-donating medium; in general, between 0° and 150° C., in particular, between 20° and 120° C. The reaction temperature also depends, in particular, on whether the work is carried out under pressure or without pressure. The reaction time, depending on the reaction mixture, reaction temperature and other reaction parameters, lies between 10 minutes and 20 hours. After completion of hydrolytic splitting, the pyrazol-1-ylphenylacetic acids are isolated according to customary methods, e.g. by recrystallization or by acidification of their solutions, optionally with concentration of their solutions. For their purification, their alkaline solution is, e.g., extracted with an organic solvent, for example diethyl ether, benzene, chlorobenzene, chloroform or methylene chloride, which is not miscible with the alkaline solution.

The conversion of pyrazol-1-ylphenylacetic acids of formula II into their salts is, e.g., effected by direct alkaline solvolysis with hydroxyl ions of the pyrazol-1-ylphenylacetic acid derivatives of formula III. As alkaline reactant, the inorganic or organic base of the desired salt is expediently used. The salts are, however, also obtained by reacting the pyrazol-1-ylphenylacetic acids of formula II with the stoichiometric equivalent of corresponding base or by converting readily-soluble salts into sparingly-soluble salts by double decomposition or by converting any desired salt into a pharmacologically-compatible salt.

In a further embodiment of the process, functional pyrazol-1-ylphenylacetic acid derivatives of formula III, in which F represents an optionally-substituted, preferably mono-substituted, benzyl ester group, and $R^1$, $R^2$, $R^3$ and $R^4$ have their previously-noted meanings, are hydrogenolytically split. This form of lyolysis of benzyl esters of formula III is carried out under standard conditions, for example with hydrogen on palladium charcoal or platinum, at −10° to 50° C., preferably at room temperature, under from 1 to 200, preferably from 1 to 10, atmospheres pressure and in an inert solvent, such as methanol, ethyl acetate or, preferably, glacial acetic acid.

In a further embodiment of the process, functional pyrazol-1-ylphenylacetic acid derivatives of formula III [in which F represents a tert. alkyl ester group with, for example, from 4 to 9 carbon atoms, preferably a tert.-butyl ester group, and $R^1$, $R^2$, $R^3$ and $R^4$ have their previously-stated meanings] are thermolytically split. This form of lyolysis of tert.-alkyl esters of formula III is carried out under standard conditions, e.g. in an inert organic solvent, for example chlorobenzene or xylene, without or, preferably, in the presence of an acid catalyst, for example p-toluenesulfonic acid, by heating to a temperature from 30° to 200° C., preferably from 70° to 150° C.

A further process for preparing pyrazol-1-ylphenylacetic acids of formula II, their salts and their functional carboxylic acid derivatives is characterized by condensing (in a manner which is known per se) a free or protected hydrazinophenylacetic acid IE, its functional carboxylic acid derivatives or its salts with a reactive C₃ fragment; where appropriate, an A⋯⋯⋯B single bond is subsequently dehydrogenated and/or the pyrazole ring is halogenated in the 4-position and/or a functional carboxylic acid derivative is lyolysed, i.e. converted into the free carboxylic acid by hydrolytic, hydrogenolytic or thermolytic splitting, and/or the obtained acids of formula II or their salts are conventionally converted into one another, i.e. a compound of formula II (in free acid form) is optionally converted into a salt, or a compound of formula II (in salt form) is optionally converted into the free acid or into another salt.

Favored compounds IE are free or protected p-hydrazinophenylacetic acids IF [wherein $R^3$ is —H, and —C($R^4$)H—COOH is meta to $R^2$ and para to Z], their functional carboxylic acid derivatives and their salts.

Preferred compounds IF are compounds IG (in which $R^2$ represents a halogen atom, preferably chloro, and $R^4$ denotes a hydrogen atom or methyl), their functional carboxylic acid derivatives and their salts.

Of the functional carboxylic acid derivatives of compounds IE, derivatives are suitable which are stable to an attack of the hydrazino group Z (thus avoiding polycondensation); these are preferably nitriles, amides and esters. The free carboxylic acids IE are preferred to their functional derivatives.

As reactive $C_3$ fragments, the optionally-($\alpha$- and/or $\beta$)-substituted derivatives [which are capable of being used in known manner for the synthesis of 3,5-unsubstituted pyrazoles or pyrazolines] of propiolaldehyde, acrylaldehyde, malonaldehyde, propionaldehyde or 1,2,3-propanetriol are used; the preparation and reaction of these derivatives are described, for example, in the following literature passages:

R. C. Elderfield, "Heterocyclic Compounds", Vol. 5, pp. 45–161 (1957), John Wiley and Sons, Inc., New York; A. R. Katritzky, "Advances in Heterocyclic Chemistry", Vol. 6, pp. 347–429 (1966), Academic Press, New York; Beilstein 23, pages 39–41, 43; ibid. 23I, p. 15; German Offenlegungsschrift No. 1,670,692; German Offenlegungsschrift No. 1,670,060; C. Reichardt et al., *Liebigs Ann. Chem.*, 737 (1970), 99; A. Dornow et al. *Chem. Ber.*, 82 (1949), 257; J. N. Wells et al., *J. Pharm. Sci.*, 1971, 533; Brit. Pat. No. 779,519; V. T. Klimko et al, *CA*, 55, 22291d (1961); USSR Pat. No. 115903 [*CA*, 53 (1959), 16170f]; USSR Pat. No. 125253 [*CA*, 54 (1960), 15413h]; T. V. Protopova et al., *CA*, 52 (1958), 12754b; ibid., *CA*, 54 (1960), 11037c and 20869f; ibid., *CA*, 58, 7825g; V. T. Klimko et al., *CA*, 58 (1963), 8890h and 9069h; E. Rothstein et al., *J. Chem. Soc.*, 1953, 4012; M. F. Shostakovskii *CA*, 56 (1962), 5808b; S. N. Danilov et al., *CA*, 52 (1958), 6191a; Netherlands Published Specification No. 6,407,462; F. Nerdel et al., *Liebigs Ann. Chem.*, 710, 36 (1967); R. Gelin et al., *Bull. Soc. Chim. France*, 1966, 2347; S. W. Tobey et al., *J. Am. Chem. Soc.*, 88 (1966), 2478; H. Bredereck et al., *Angew. Chem.*, 77 (1965), 219; Z. Arnold, *CA* 53 (1959) 4120i, *CA*, 56 (1962) 15328g, *CA*, 63 (1965) 5522c; Z. Arnold et al., *CA*, 54 (1960), 1274b; D. Lloyd et al., *Angew Chem.* 88 (1976), 496.

For the synthesis of pyrazoles, for example, the following reactive $C_3$ fragments are suitable:

propiolaldehyde and its derivatives, such as propiolaldehydedimethylacetal or propiolaldehydedibutylacetal;

$\alpha$-substituted acrylaldehydes and their derivatives, for example 2-haloacrylaldehydes, such as 2-chloroacrylaldehyde; 2-bromoacrylaldehyde or 2-chloroacrylaldehydedimethylacetal;

$\beta$-substituted acrylaldehydes and their derivatives, for example 3-hydroxyacrylaldehyde (enol of malondialdehyde); 3-haloacrylaldehydes, such as 3-chloro- or 3-bromoacrylaldehyde; 3-alkoxyacrylaldehydes, such as 3-methoxy-, 3-ethoxy- or 3-butoxy-acrylaldehyde; 3-aryloxyacrylaldehydes, such as 3-phenoxyacrylaldehyde; 3-aralkoxyacrylaldehydes, such as 3-benzyloxyacrylaldehyde; 3-acyloxyacrylaldehydes, such as 3-acetoxyacrylaldehyde, 3-benzoyloxyacrylaldehyde, 3-tosyloxyacrylaldehyde, 3-methoxycarbonyloxyacrylaldehyde, 3-benzyloxycarbonyloxyacrylaldehyde, 3-ethoxycarbonyloxyacrylaldehyde, 3-phenoxycarbonyloxyacrylaldehyde; 3-aminoacrylaldehyde and N-substituted derivatives, such as 3-(N,N-dimethylamino)acrylaldehyde, 3-(N,N-diethylamino)acrylaldehyde, 3-piperidinoacrylaldehyde, 3-anilinoacrylaldehyde, 3-(N-methylanilino)acrylaldehyde; 3-ethoxyacrylaldehydediethylacetal; 1,3,3-trichloropropene, 3-(N,N-dimethylamino)acrylaldehydedimethylacetal; 1-methoxy-3-(N-methyl-N-phenyliminio)propene methylsulfate, 1-methylamino-3-dimethyliminiopropene methylsulfate, 1-methylamino-3-methyliminiopropene chloride, 1-dimethylamino-3-dimethyliminiopropene perchlorate, 1-dimethylamino-3-phenyliminopropene, 1-dimethylamino-3-($\alpha$-pyridyl)iminopropene, 1-anilino-3-phenyliminopropene, 1-(N-methylanilino)-3-(N-methyl-N-phenyliminio)propene perchlorate; malondialdehyde and its derivatives, for example 1,1,3,3-tetramethoxypropane, 1,1,3,3-tetraethoxypropane, 1,3-dichloro-1,3-dimethoxypropane, 1,3-dichloro-1,3-diethoxypropane, 3,3-dichloropropionaldehyde, 3-bromo-3-methoxypropionaldehyde, 1,1,3-tribromo-1-acetoxypropane, 1,1-dibromo-3,3-dimethoxypropane, 1,3-diacetoxy-1,3-diethoxypropane, 1,3-diacetoxy-1,3-dibutoxypropane, 1,1,3,3-tetrachloropropane, 1,1,3,3-tetrakis(methylthio)propane, 1,1-dimethoxy-3,3-bis(methylthio)propane;

$\alpha,\beta$-disubstituted acrylaldehydes and their derivatives, for example 2-bromo-3-methoxyacrylaldehyde, 2-bromo-3-acetoxyacrylaldehyde, 2-bromo-3-benzoyloxyacrylaldehyde, 2-chloro-3-benzoyloxyacrylaldehyde, 2-chloro-3-anilinoacrylaldehyde, 2-chloro-3-(N-methylanilino)acrylaldehyde, 2-chloro-3-dimethylaminoacrylaldehyde, 2-fluoro-3-dimethylaminoacrylaldehyde, 2,3-dichloroacrylaldehydedimethylacetal, 1-anilino-2-chloro-3-phenyliminopropene, 1-anilino-2-bromo-3-phenyliminopropene, 1-anilino-2-iodo-3-phenyliminopropene, 2-chloro-1-dimethylamino-3-dimethyliminiopropene perchlorate, 1,2,3,3-tetrachloropropene;

substituted malondialdehydes and their derivatives, for example chloromalondialdehyde, bromomalondialdehyde, fluoromalondialdehyde, iodomalondialdehyde, 3,3-diethoxy-2-chloropropionaldehyde, 1,1,3,3-tetraethoxy-2-chloropropane, 1,1,3,3-tetraethoxy-2-bromopropane, 1,3-diethoxy-1,2,3-trichloropropane, 2-bromo-1,1,3,3-tetrakis(methylthio)propane, 3,3-diethoxy-2-bromopropionaldehyde;

$\alpha,\beta$-disubstituted propionaldehydes and their derivatives, for example 2,3-dibromopropionaldehyde, 2,3-dibromopropionaldehydediethylacetal, 2,3-dichloropropionaldehydediethylacetal, 3-ethoxy-2-chloropropionaldehydediethylacetal, 3-ethoxy-2-bromopropionaldehydediethylacetal, 1,3,3-trisacetoxy-2-chloropropane.

For the synthesis of pyrazolines, for example, the following reactive $C_3$ fragments are suitable:
acrylaldehyde and its derivatives, for example acrylaldehydedimethylacetal, acrylaldehydediethylacetal;
β-substituted propionaldehydes and their derivatives, for example 3-chloropropionaldehyde, 3-dimethylaminopropionaldehyde, 3-ethoxypropionaldehydediethylacetal, 3-bromopropionaldehyde-ethylene-acetal;
1,2,3-propanetriol derivatives, for example 2,3-dichloro-1-propanol,1,3-dichloro-2-propanol, 1,2,3-tribromopropane, 3-chloro-1,2-epoxypropane.

The reaction of hydrazinophenylacetic acids IE, their functional carboxylic acid derivatives or their salts with a reactive $C_3$ fragment is carried out under solvent-free conditions, in water or in a non-aqueous inert solvent (optionally in the presence of water) at temperatures between $-20°$ C. and $200°$ C., preferably at from $10°$ to $150°$ C., at atmospheric pressure or, if desired, in a closed vessel at elevated pressure. Suitable inert solvents are, for example, alcohols, such as methanol or ethanol; ethers, such as diethyl ether, ethyleneglycolmonoethyl ether or dioxan; amides, such as formamide, dimethylformamide or N-methylpyrrolidone; lower aliphatic carboxylic acids, such as glacial acetic acid; hydrocarbons or chlorohydrocarbons. The reaction proceeds without a proton donor but is, as a rule, catalyzed by a proton donor, which is used in a catalytic amount or even in molar excess, for example with the use of glacial acetic acid or semi-concentrated hydrochloric acid as solvent.

Reaction times are governed by the reactants, the reaction medium and the reaction temperature and are, as a rule, from 0.5 to 15 hours. The hydrazino compound and the $C_3$-fragment compound are ordinarily used in equivalent amounts, but it is often of advantage to use the less expensive component, usually the reactive $C_3$ fragment, in an excess of from about 5 to 20%. The reactive $C_3$ fragment used may undergo (during the reaction) a—mostly hydrolytic—conversion into a different reactive $C_3$ fragment. For example, functional derivatives of aldehyde groups, such as acetals, acylates or geminal dihalides, readily hydrolyze into the aldehyde function in a strongly acid aqueous medium. As is known, the condensation of hydrazines with reactive $C_3$ fragments proceeds via intermediate steps which, often, cannot be isolated. Hydrazones or 4- or 5-substituted pyrazolines are optional intermediates, from which pyrazoles are formed through splitting off of, for example, water, halogen hydride, alcohols or amines under reaction conditions.

If, by means of a reactive $C_3$ fragment, a pyrazoline is prepared, the latter, during the reaction, is readily dehydrogenated or oxidized into pyrazoles by atmospheric oxygen or by the reactants. When such a reaction is not desired, atmospheric oxygen is excluded.

A further process for the preparation of pyrazol-1-ylphenylacetic acids of formula IB wherein
$R^1$ is in the 4-position and represents halo, preferably chloro or bromo; and
$R^2$, $R^3$ and $R^4$ have their previously-noted meanings, their salts and their functional carboxylic acid derivatives, comprises halogenating a pyrazol-1-ylphenylacetic acid of formula IB [which (in the pyrazole ring) is unsubstituted or is substituted by a diazonium group, that is a pyrazol-1-yl-phenylacetic acid of formula IB wherein $R^1$ is in the 4-position and represents a hydrogen atom or $N_2^+$, and $R^2$, $R^3$ and $R^4$ have their previously-noted meanings], its salts or its functional carboxylic acid derivatives. Halogenation is effected in known manner, i.e. reaction with a halogenating agent. Subsequently, the halogenated product is optionally lyolyzed and/or the obtained acids of formula IB are converted into salts or their salts are converted into other salts or into the corresponding free acid.

Preferred products of the halogenation are compounds of formula IC in which $R^1$ represents halo, preferably chloro or bromo; and $R^2$, $R^3$ and $R^4$ have their previously-ascribed meanings.

Particularly preferred products of the halogenation are compounds of formula ID in which $R^1$ represents halo, preferably chloro or bromo; and $R^2$ and $R^4$ have their previously-stated meanings, $R^2$ preferably representing bromo and, more particularly, chloro, and $R^4$ preferably representing a hydrogen atom or methyl.

Suitable halogenating agents for pyrazol-1-ylphenylacetic acids (which are unsubstituted in the pyrazole ring) are, for example, compounds mentioned in Houben-Weyl ["Methoden der Organischen Chemie", Thieme Verlag, Volume 5/3, pp. 511 to 960 (1962) and Volume 5/4, pp. 233 to 316 and pp. 557 to 593 (1960)] or in A. R. Katritzky ["Advances in Heterocyclic Chemistry", Vol. 6, pp. 391 to 396 (1966), Acad. Press, New York], e.g. the free halogens (chlorine, bromine and iodine), salts and esters of hypohalous acids, N-halogenamides and N-halogenimides, sulfuryl chloride, phosphorus pentachloride or iodine chloride. The reaction with the halogenating agent is carried out in known manner in aqueous medium (e.g. with sodium hypochlorite) or in an inert non-aqueous solvent, such as a chlorinated hydrocarbon or glacial acetic acid (e.g. with chlorine, bromine, iodine or sulfuryl chloride), at temperatures of from $-20°$ to $120°$ C., preferably at from $0°$ to $80°$ C., with excess or, preferably, equivalent amounts of the halogenating agent. The reaction is, as a rule, complete in from 0.5 to 2 hours after addition of the halogenating agent.

Suitable halogenating agents for pyrazol-1-ylphenylacetic acids which are substituted in the pyrazole ring by a group $N_2^+$ are, for example, halogen compounds mentioned in Houben-Weyl ["Methoden der Organischen Chemie", Thieme Verlag, Volume 5/3, pp. 213 to 245, 846 to 853; Volume 5/4 pp. 437 to 451, 639 to 647], for example anhydrous hydrofluoric acid, concentrated tetrafluoroboric acid, hydrochloric acid, hydrobromic acid or hydriodic acid, as a rule in excess, and, where appropriate, in the presence of catalyst, for example copper, copper (I) chloride, copper (II) chloride or copper (I) bromide. Reaction temperatures ordinarily lie between $10°$ and $150°$ C., preferably at the boiling temperature of the solvent in which the reaction is effected.

The starting compounds, i.e. pyrazol-1-ylphenylacetic acids of formula II (their derivatives and their salts), which are substituted in the pyrazole ring by an $N_2^+$ group, are obtained, for example, by nitrating (in known manner) a compound of formula II which is unsubstituted in the pyrazole ring, reducing the nitro group and diazotizing the thus-formed amino group with nitrous acid. Likewise, condensation of hydrazino compounds IE and their derivatives in known manner with nitromalondialdehyde, nitrosomalondialdehyde or acylaminomalondialdehyde results in the preparation of the corresponding 4-nitro-, 4-nitroso- or 4-acylaminopyrazol-1-ylphenylacetic acid derivatives, which are converted into the corresponding 4-amino compounds by reduction or hydrolysis.

The hydrazinophenylacetic acids IE, their derivatives and their salts, which serve as starting compounds, are obtained from the appropriate amino compounds by diazotization, or from the appropriate acylamino compounds, preferably the acetylamino compounds, by nitrosation and subsequent reduction of the formed diazoniumphenylacetic acids (their derivatives and their salts) or the N-nitroso-N-acylaminophenylacetic acids (their derivatives and their salts). The preparation of the diazonium compounds and N-nitroso-N-acylamino compounds is carried out in a manner which is known per se (cf. "Houben-Weyl", Volume 10/3, pp. 1 to 213).

The reduction of the diazonium salts, the diazotates or the N-nitroso-N-acylamino compounds is effected with the usual reducing agents (cf. "Houben-Weyl", Volume 10/2, pp. 177 to 223). For example, the reduction is carried out in strongly-acid solution with tin(II) chloride, in weakly-alkaline to weakly-acid aqueous or alcoholic solution with sodium sulfite, sodium hydrogen sulfite or $SO_2$ solutions; where appropriate, the primarily-resulting $\beta$-monosulfonic acid derivatives or $\alpha,\beta$-disulfonic acid derivatives of the hydrazinophenylacetic acids (their derivatives and their salts) are hydrolyzed in one reaction step into the corresponding hydrazinophenylacetic acids (their derivatives and their salts).

Besides the aforesaid agents, iron, zinc, endiols in weakly-acid solution and sodium amalgams in alkaline solution are useful as reducing agents.

The reducing agents are used in equimolar amounts and, where appropriate, also in excess. For the reduction, the reduction temperatures lie in the range of from $-10°$ to $+10°$ C.; the reaction times lie in the range of from 5 to 120 minutes.

For the hydrolytic splitting of the sulfonic acid derivatives, the reaction temperatures lie in the range from room temperature to the boiling temperature of the solvent, preferably at from 80° to 100° C., and the reaction times are from 0.5 to 24 hours.

The isolation of the hydrazinophenylacetic acids is effected in the form of sparingly-soluble salts, expediently the arylsulfonates, preferably the p-toluenesulfonates. For further processing of the hydrazinophenylacetic acids into compounds of formula II, it is advantageous to use the reaction solution directly for reaction with a reactive $C_3$ fragment.

Further, the hydrazinophenylacetic acids are obtained directly from corresponding aminophenylacetic acids through reaction with hydroxylamino-O-sulfonic acid in a manner which is known per se ("Houben-Weyl", Volume 10/2, pp. 297 to 298). The reaction is expediently carried out in an aqueous system containing alkali-metal (e.g. sodium), hydroxide or excess, for example double the molar amount, of aminophenylacetic acid, at temperatures of from 60° to 100° C. The reaction times are from 0.5 to 2 hours.

The hydrazinophenylacetic acids IE, their derivatives and salts are new compounds with the exception of 4-hydrazinophenylacetic acid.

The functional pyrazol-1-ylphenylacetic acid derivatives of compounds of formula II (used as starting or intermediate products) are prepared according to known methods. Thus, the nitriles are obtained from the appropriate halomethyl compounds, and alkali-metal cyanides or alkaline-earth-metal cyanides, expediently in an aprotic dipolar solvent or in a two-phase system in the presence of a phase transfer catalyst, such as benzyl-trimethylammonium chloride, at temperatures of from 0° to 80° C.; further, by reaction of an unsubstituted amide with a dehydrating agent, for example phosphorus oxychloride, phosphorus pentoxide or thionyl chloride.

Pyrazol-1-ylphenylacetic acid esters of compounds of formula II are readily accessible according to known methods from other reactive acid derivatives, e.g. acid halides, acid anhydrides and nitriles, of compounds of formula II through alcoholysis; further, by reacting a free acid of formula II with an alcohol under conditions in which water is split off, or by reacting an acid or salt (e.g. an alkali-metal salt) with an alkylating agent (e.g. a benzyl halide) to produce the corresponding benzyl ester.

Unsubstituted amides of compounds of formula II are prepared, for example, by alkaline or acid hydrolysis of appropriate nitriles. The aminolysis of reactive carboxylic acid derivatives, such as acid halides or esters, with ammonia, with mono- and di-alkylamines, with arylamines, with cyclic amines (such as piperidine, morpholine and piperazine), with hydroxylamine, with O-alkyl-hydroxylamine and with optionally-substituted hydrazines, yields corresponding N-alkyl-substituted or aryl-substituted amides, piperidides, morpholides or piperazides; further, hydroxamic acids, N-alkoxyamides and, where appropriate, N-alkyl-substituted or aryl-substituted hydrazides of compounds of formula II. The reaction of acid halides with mercaptans gives thioesters.

Thioamides of compounds of formula II are, for example, prepared by reaction of nitriles and hydrogen sulfide in the presence of or in media containing base or by sulfurization of amides, for example with phosphorus pentasulfide.

With acid catalysis nitriles of compounds of formula II add on alcohols to yield appropriate carboximidates; with basic catalysis the nitriles add on arylamines to yield appropriate amidines; and the nitriles add on mercaptans or mercaptoacetic acid to yield appropriate thiocarboximidates.

Reaction of carboximidates or of imidoyl halides of compounds of formula II with amines yields amidines; with $\beta$-amino alcohols, oxazolines; and with $\beta$-diamines, imidazolines.

Acid halides of compounds of formula II are prepared in known manner by reacting corresponding free acids of formula II or their salts with a halide of phosphoric or sulfuric acid or by halogenating the corresponding acid hydrazide; and corresponding ketenes are prepared from the acid halides by dehydrohalogenation by means of tertiary base.

A further process for preparing pyrazol-1-ylphenylacetic acids IB, their functional carboxylic acid derivatives and their salts is characterized by dehydrogenating a pyrazolin-1-ylphenylacetic acid of formula II (wherein $R^1$ denotes a hydrogen atom, and A┄┄┄┄B denotes a carbon—carbon single bond), a functional carboxylic acid derivative or a salt thereof and, where appropriate, halogenating the pyrazole ring in the 4-position and/or lyolyzing a functional carboxylic acid derivative, i.e. converting it into the corresponding free carboxylic acid by hydrolytic, hydrogenolytic or thermolytic splitting, and/or converting the obtained acid of formula II into one of its salts or the obtained salt into a different salt or into the corresponding free acid in customary manner. When desired, a compound of formula II (obtained in free-acid form) is converted into a salt, or a salt of a compound of formula II is converted into the corresponding free acid or into another salt.

Dehydrogenation of pyrazolin-1-ylphenylacetic acids of formula II, their functional derivatives and their salts is effected according to known methods (e.g. Katritzky, loc. cit., pp. 385 to 387) by reaction with a dehydrogenating or oxidizing agent. Such agents include, for example, metal catalysts, such as platinum or palladium, which, at elevated temperature, cause a splitting off of hydrogen; further, hydrogen acceptors, such as tetrachloro-p-benzoquinone, or oxidizing agents, such as activated manganese dioxide, potassium permanganate, lead dioxide, bromine or sulfur, which are used in at least molar amounts. The reaction is carried out in an inert solvent, for example toluene, methylene chloride or dimethylformamide, at temperatures of from 0° to 120° C., preferably at boiling temperatures; the conditions depend on the dehydrogenating or oxidizing agent used.

A further process for preparing a pyrazol- or pyrazolin-1-ylphenylacetic acid of formula II (wherein $R^4$ denotes an alkyl group), a functional carboxylic acid derivative or a salt thereof, is characterized by reacting a corresponding pyrazol-1-ylphenylacetic acid or pyrazolin-1-ylphenylacetic acid of formula II (which is unsubstituted in α-position, i.e. wherein $R^4$ represents a hydrogen atom), a functional carboxylic acid derivative or a salt thereof with an alkylating agent and, where appropriate, an A┄┄┄B single bond is subsequently dehydrogenated and/or the pyrazole ring is halogenated in the 4-position and/or a functional carboxylic acid derivative is lyolysed, i.e. converted into the corresponding free carboxylic acid by hydrolytic, hydrogenolytic or thermolytic splitting, and/or the obtained free acid of formula II is conventionally converted into a salt, or the obtained salt of a compound of formula II is conventionally converted into the corresponding free acid or into another salt.

The reaction of an α-substituted pyrazol-1-ylphenylacetic acid of formula II, a functional carboxylic acid derivative or a salt thereof with an alkylating agent is effected according to known and well-established methods.

Suitable alkylating agents are, for example, compounds $R^4Q$, in which $R^4$ denotes an alkyl group, preferably with from 1 to 5 carbon atoms, more particularly with 1 or 2 carbon atoms and, advantageously, with one carbon atom, and Q denotes the radical of a strong acid, such as a halogen atom or an alkyloxysulfonyl or arylsulfonyl group. Alkylation is, as a rule, carried out at temperatures between −80° and 150° C., preferably between 0° and 100° C., under solvent-free conditions or, preferably, in an inert solvent, in a one-phase or two-phase system in the presence of or in contact with a basic condensation agent. Suitable solvents are, for example, aromatic hydrocarbons, such as benzene or toluene (where appropriate, also in the presence of water in a two-phase system); alcohols, such as ethanol or 2-methoxyethanol; ethers, such as diethyl ether or tetrahydrofuran; or aprotic dipolar solvents, such as dimethylformamide, N-methylpyrrolidone, dimethylsulfoxide or sulfolane. Suitable basic condensation agents are, for example, alkali metals or alkaline-earth metals; their hydroxides, hydrides, amides, dialkylamides or carbonates; organic nitrogen bases, such as pyridine or triethylamine; or phase transfer catalysts, e.g. quaternary organic nitrogen or phosphorus compounds, such as triethylbenzylammonium chloride or hexadecyltributylphosphonium bromide, in the presence of alkali-metal hydroxides.

The alkylating agent and the basic condensation agent are, as a rule, used in 1- to 1.2-fold molar excess. In the case of the alkylation of a free α-unsubstituted pyrazol-1-ylphenylacetic acid, the dianion is prepared with 2 moles of a strong base, e.g. lithium diisopropylamide, at from −70° to −80° C. and the α-carbon atom is selectively alkylated at increasing temperature.

A further process for the preparation of pyrazol-1-ylphenylacetic acids of the formula II

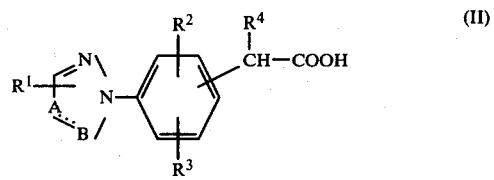

wherein each of
$R^1$, $R^2$ and $R^3$ is, independently, a hydrogen atom (—H) or halo,
$R^4$ is a hydrogen atom or alkyl (preferably lower alkyl), and
A┄┄┄B denotes two carbon atoms bound together by either a single or a double bond,
their functional carboxylic acid derivatives and their salts, is characterised by reacting a pyrazol-1-ylphenylacetic acid of the formula IV

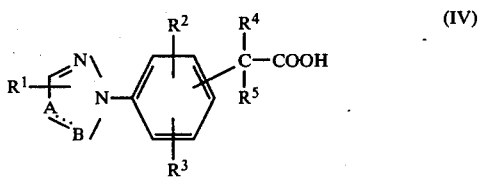

wherein
$R^1$, $R^2$, $R^3$, $R^4$ and A┄┄┄B have their previously-ascribed meanings, and
$R^5$ denotes alkanoyl, alkoxycarbonyl, cyano or alkyloxalyl, its functional carboxylic acid derivatives or its salts with an alkali metal hydroxide in organic, organic-aqueous or aqueous medium or, when $R^5$ does not have the meaning of cyano, with an alkali metal alkanolate in anhydrous medium or, when $R^5$ does not have the meaning of alkanoyl, also with an aqueous mineral acid; by liberating from the alkali metal salt of a dicarboxylic acid [which is optionally obtained as intermediate when an alkali metal hydroxide is used] the dicarboxylic acid V

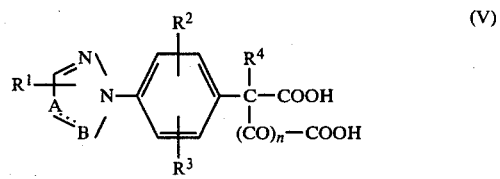

wherein $R^1$, $R^2$, $R^3$, $R^4$ and A⸺B have their previously-ascribed meanings, and n denotes 0 or 1, and heating until the equimolar amount of carbon dioxide and optionally carbon monoxide is split off; and subsequently, where appropriate, dehydrogenating an A⸺B single bond and/or halogenating the pyrazole ring in 4-position and/or α-alkylating and/or converting the obtained acids of the formula II or their salts into one another.

Suitable as alkanoyl, alkoxycarbonyl and alkyloxalyl groups are, inter alia, those with up to 6, preferably with up to 3, carbon atoms, inclusive.

Preferred starting compounds are those of the formula IV'

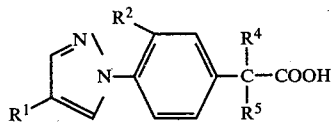

(IV')

wherein $R^1$, $R^2$, $R^4$ and $R^5$ have their previously-ascribed meanings, their benzyl and alkyl esters, their nitriles and salts.

The reactions with alkali metal hydroxides, in particular sodium or potassium hydroxides, are preferably carried out under heating. If the desired process products are compounds of the formula II, in which A⸺B denotes a single bond, the process is to be carried out under exclusion of oxygen, e.g. in $N_2$ atmosphere. As reaction medium there serves e.g. a low-molecular-weight alkanol, such as methanol, ethanol, isopropanol or n-butanol; further, an alkanediol or a monoalkyl ether thereof e.g. ethyleneglycol, 2-methoxyethanol or 2-ethoxyethanol; where appropriate, water is added to the said solvents in the volume ratio of 10:1 to 1:2. Further, as reaction medium there may also be used water or e.g. a mixture of water with water-soluble ethereal solvents such as dioxan or tetrahydrofuran.

In the case of reactons of malonic acid dialkyl esters, acetoacetic acid alkyl esters or alkyloxalylacetic acid alkyl esters of formula IV with alkali metal alkanolates there is preferably present the same low-molecular-weight alkanol, e.g. methanol, ethanol, n-butanol, as component of the starting ester and of the alkanolate and as reaction medium.

However, it is also possible [by use of a relatively higher-boiling alkanol (not identical with the low-molecular-weight alkanol present as ester component) as reaction medium and distillation of a part thereof] to carry out a transesterification simultaneously with the reaction or to accept a partial transesterification and then to hydrolyse to give the appropriate acid. Further, as reaction medium there are also used, instead of a low-molecular-weight alkanol, e.g. an inert organic solvent, such as e.g. benzene or toluene. The reaction is carried out at room temperature or elevated temperature, e.g. at boiling temperature of the reaction medium used.

For the reaction of starting compounds of the formula IV or IV', in which $R^5$ does not have the meaning of alkanoyl, with an aqueous mineral acid, the usual mineral acids such as sulphuric acid, phosphoric acid or hydrochloric acid are suitable.

Whereas in the case of the reaction with alkali metal hydroxides under severe reaction conditions, e.g. in a boiling mixture of ethylene glycol with a little water, salts of monocarboxylic acids of the general formula II are formed directly, there are obtained under milder conditions, e.g. with much water or in low alkanols or at low temperatures, initially salts of dicarboxylic acids. From the latter, according to the process the appropriate dicarboxylic acids of the general formula V or V' are liberated, e.g. by reaction of the alkali metal salts with the equivalent amount of a mineral acid such as hydrochloric acid.

Preferred representatives of the intermediate products V are those of the formula V'

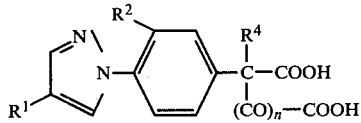

(V')

wherein $R^1$, $R^2$, $R^4$ and n have their previously-ascribed meanings, and their alkali metal salts.

The intermediate products of the general formula V or V' are also prepared by hydrogenolysis of the appropriate dibenzyl esters or by mild acid hydrolysis of appropriate di-tert.-butyl esters.

A variant of the conversion of pyrazol-1-ylphenylacetic acids of the formula IV or IV', their functional derivatives and salts into pyrazol-1-ylphenylacetic acids of the formula II and their salts therefore encompasses a reaction according to which a compound of the formula V or V' is heated until an equimolar amount of carbon dioxide and optionally carbon monoxide is split off in the presence or absence of a catalyst and a solvent or diluent and subsequently, where appropriate, an A⸺B single bond is dehydrogenated and/or the pyrazole ring is halogenated in 4-position and/or α-alkylated and/or an obtained free carboxylic acid of the formula II is converted into a salt.

The starting compounds of the formula IV or IV' are obtained e.g. by condensation of pyrazol-1-ylphenylacetic acids of the formula II or [wherein $R^4$ represents a hydrogen atom and the other substituents have their previously-ascribed meanings, their benzyl or alkyl esters, their nitriles or salts] with dibenzyl or dialkyl carbonates, oxalic acid dibenzyl esters or oxalic acid dialkyl esters or acetic acid alkyl esters, wherein alkyl in each case denotes an alkyl group with 1 to 5 carbon atoms, in the presence of alkali metal alkanolates. The obtained compounds of the formula IV or IV', in which $R^4$ is a hydrogen atom, are, if desired, converted by alkylation into intermediate products of the formula IV or IV' wherein $R^4$ denotes an alkyl group, preferably a methyl or ethyl group. The alkylation is effected according to processes known per se, e.g. by reaction with an alkylating agent $R^4Q$, wherein $R^4$ and Q have their previously-ascribed meanings, in the presence of a basic condensation agent.

A further process for the preparation of pyrazol-1-ylphenylacetic acids of the formula II

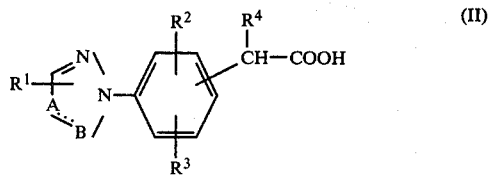

wherein each of
- $R^1$, $R^2$ and $R^3$ is, independently, a hydrogen atom (—H) or halo,
- $R^4$ denotes a hydrogen atom or alkyl, and
- A········B denotes two carbon atoms bound together by either a single or a double bond, their functional carboxylic acid derivatives and their salts, is characterised by reducing a pyrazol-1-ylphenylacetic acid of the formula VI

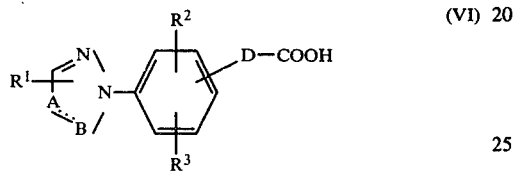

wherein
- D denotes $>C=O$, $>C(OH, R^4)$ or $>C(Oalk, R^4)$ and alk denotes alkyl, e.g. with 1 to 4 carbon atoms, and
- $R^1$, $R^2$, $R^3$, $R^4$ and A········B have their previously-ascribed meanings, its functional carboxylic acid derivatives or its salts and subsequently, where appropriate, dehydrogenating an A········B single bond and/or halogenating the pyrazole ring in 4-position and/or lyolysing a functional carboxylic acid derivative, i.e. converting by hydrolytic, hydrogenolytic or thermolytic splitting into the free carboxylic acid, and/or α-alkylating and/or converting the obtained acids of the formula II or their salts into one another.

Preferred starting compounds of the formula VI are pyrazol-1-ylphenylacetic acids of the formula VI′

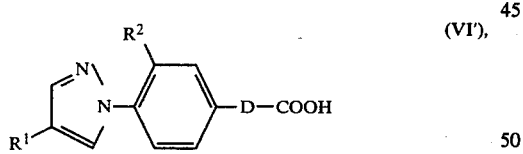

wherein $R^1$, $R^2$ and D have their previously-ascribed meanings, and their salts.

The reduction of the pyrazolylphenylacetic acids VI or VI′ is effected according to processes known per se. The reduction of the pyrazolylphenylglyoxylic acids VI or VI′ (D=>C=O) is for example so carried out that the compounds VI or VI′ are reacted with hydrazine and the obtained hydrazone is heated in the presence of alkali metal alkanolates or hydroxides. The reaction is preferably carried out as one-pot process, i.e. carried out without isolation of the hydrazone. When the reaction is effected at normal pressure, the usual solvents, particularly high-boiling solvents, e.g. diglycol or triglycol, are used as reaction medium. If the reaction is carried out in an autoclave, i.e., under pressure, for example low alcohols, e.g. butanols or pentanols, are used as reaction medium. The reaction temperatures lie preferably between 150° and 240° C. The reduction of the pyrazolylphenylhydroxyacetic acids VI or VI′ [D=>C(OH, $R^4$)] is for example carried out with tin(II) chloride in a mixture of hydrochloric acid and acetic acid, with iodine and phosphorus in glacial acetic acid or with hydrogen iodide, optionally in the presence of red phosphorus. The reduction of the pyrazolylphenylalkoxyacetic acids VI or VI′ [D=>C(O-alk, $R^4$)] is for example carried out catalytically with a noble metal catalyst such as Pd/carbon at room temperature or elevated temperature, at normal pressure or increased pressure, e.g. 2–10 atm, preferably in the presence of strong acids, such as perchloric acid, in solvents usual in hydrogenations, e.g. glacial acetic acid. The reduction is preferably carried out at elevated temperatures, e.g. at the boiling temperature of the reaction medium.

The starting compounds of the formula VI are obtained according to processes known to one skilled in the art. For example, the pyrazolylphenylglyoxylic acids VI or VI′ are obtained by hydrolysis, oxidation and lyolysis of appropriate α-chloropyrazolylphenylacetic acid esters. The reduction of the pyrazolylphenylglyoxylic acids yields the pyrazolylphenylmandelic acids VI or VI′ [D=>CH(OH)] which, if desired, are converted by alkylation into the pyrazolylalkoxyacetic acids [D=>CH(O-alk)]. The pyrazolylphenylhydroxyacetic acids VI or VI′ [D=>$CR^4$(OH)] are obtained from the appropriate pyrazolylphenyl alkyl ketones, e.g. the pyrazol-1-yl-acetophenones or -propiophenones, by addition of hydrogen cyanide and hydrolysis of the obtained cyanhydrins. Alkylation of these hydroxy compounds leads to the alkoxy compounds [D=>$CR^4$(O-alk)].

A further process for the preparation of pyrazol-1-ylphenylacetic acids of the formula II

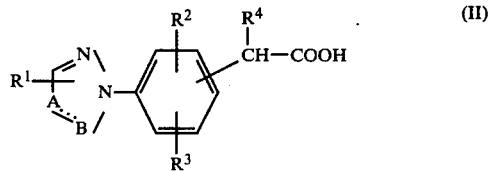

wherein each of
- $R^1$, $R^2$ and $R^3$ is, independently a hydrogen atom (—H) or halo,
- $R^4$ denotes a hydrogen atom or alkyl, and
- A········B denotes two carbon atoms bound together by either a single or a double bond, and their salts, is characterised by decarbonylating a pyrazol-1-ylphenyl-2-oxopropionic acid of the formula VII

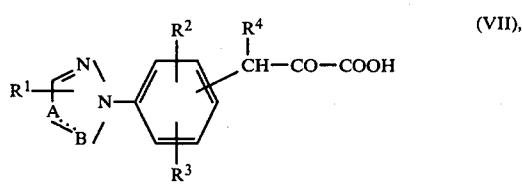

wherein $R^1$, $R^2$, $R^3$, $R^4$ and A········B have their previously-ascribed meanings, or its salts and subsequently, where appropriate, dehydrogenating an A········B single bond and/or halogenating the pyrazole ring in 4- position and/or α-alkylating and/or converting the obtained acids or their salts into one another.

Preferred starting compounds of the formula VII are pyrazolylphenyloxopropionic acids of the formula VII′

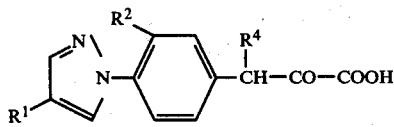

(VII′)

wherein R¹, R² and R⁴ have their previously-ascribed meanings, and their salts.

The decarbonylation of the compounds VII or VII′ is effected according to methods known per se. For example, the starting compounds VII or VII′ are heated in alcohols, such as methanol, ethanol, or water or mixtures of water and alcohols in the presence of alkali metal hydroxides, e.g. sodium or potassium hydroxide, preferably at the boiling temperature of the solvent. Optionally the acids VII or VIII′ are prepared beforehand or intermediately from their carboxylic acid derivatives, e.g. their esters or nitriles. In a preferred preparation, hydrolysis [of esters or nitriles] and decarbonylation are carried out in one step (one-pot reaction).

The starting compounds VII or VII′ are obtained for example by reaction of the appropriate pyrazol-1-ylbenzaldehydes or pyrazol-1-ylphenyl alkyl ketones with monochloroacetic acid esters or nitrile to give the appropriate ethylene oxides and their re-arrangement in the presence of Lewis acid catalysts, such as aluminium chloride, boron trifluoride etherate, zinc chloride. The pyrazol-1-ylbenzaldehydes or pyrazol-1-ylphenyl alkyl ketones are obtained from fluoro- or chloro-benzaldehydes or fluoro- or chloro-phenyl alkyl ketones, preferably the 4-fluoro- or 4-chloro-derivatives, with the sodium salt of an appropriate pyrazole, e.g. sodium pyrazolide [=pyrazol-1-yl-sodium].

A further process for the preparation of pyrazol-1-ylphenylacetic acids of the formula II

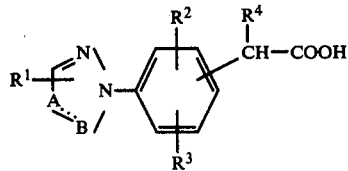

(II)

wherein each of
R¹, R² and R³ is, independently, a hydrogen atom (—H) or halo,
R⁴ denotes alkyl, and
A⋯⋯B denotes two carbon atoms bound together by either a single or double a bond,
and their salts, is characterised by hydrogenating an alkylidenpyrazolylphenylacetic acid of the formula VIII

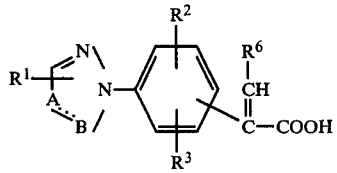

(VIII)

wherein
R¹, R², R³ and A⋯⋯B have their previously-ascribed meanings, and
R⁶ represents a hydrogen atom or alkyl, for example with 1 to 4 carbon atoms,
or its salts, and subsequently, where appropriate, dehydrogenating an A⋯⋯B single bond and/or halogenating the pyrazole ring in 4-position and/or converting the obtained acid or its salts into one another.

Preferred starting compounds VIII are alkylidenpyrazolylphenylacetic acids of the formula VIII′

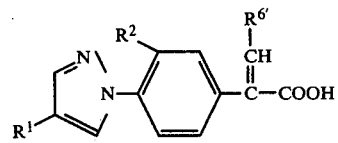

(VIII′)

wherein
R¹ and R² have their previously-ascribed meanings, and R⁶′ represents a hydrogen atom or methyl, and their salts.

The hydrogenation of the compounds VIII or VIII′ is effected according to methods known to one skilled in the art, e.g. with catalytically activated hydrogen (until the uptake of the substantially equimolar amount) or nascent hydrogen. For example, a compound of the formula VIII or VIII′ is hydrogenated in the presence of a noble metal catalyst, such as platinum on carbon, in glacial acetic acid or ethanol at normal pressure or moderately increased pressure, or such a compound is reduced by means of sodium and a low-molecular-weight alkanol or by means of sodium amalgam and water.

The starting compounds VIII or VIII′ are prepared e.g. by reaction of suitable substituted pyrazolylphenylglyoxylic acids or their salts with alkylmagnesium bromides, preferably methyl- or ethyl-magnesium bromide, and subsequent splitting off of water, e.g. by heating with mineral acids. Alternatively, they are prepared from the appropriate pyrazol-1-ylphenyl alkyl ketones, e.g. the pyrazol-1-yl-acetophenones or -propiophenones, by addition of hydrogen cyanide, hydrolysis of the obtained cyanhydrins to give the appropriate hydroxycarboxylic acids and subsequent splitting off of water by heating in mineral acids. Compounds of the formula VIII or VIII′, in which R⁶ or R⁶′ represent a hydrogen atom are also prepared from appropriate amino-atropic acids by diazotisation and reduction to hydrazino-atropic acids and their subsequent reaction with an appropriate C₃ fragment.

A further process for the preparation of pyrazol-1-ylphenylacetic acids of the formula II

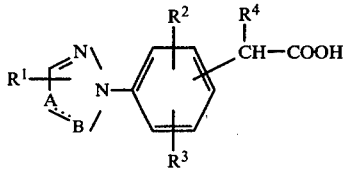

(II)

wherein each of

R$^1$, R$^2$ and R$^3$ is, independently, a hydrogen atom (—H) or halo,

R$^4$ denotes a hydrogen atom or alkyl, and

A⋯⋯B denotes two carbon atoms bound together by either a single or a double bond, and their salts, is characterised by oxidising a pyrazol-1-ylphenylmethyl derivative of the formula IX

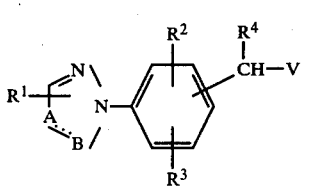

(IX)

wherein

R$^1$, R$^2$, R$^3$, R$^4$ and A⋯⋯B have their previously-ascribed meanings, and V represents an carboxaldehyde (—CHO) or hydroxymethyl (—CH$_2$OH) group, and subsequently, where appropriate, dehydrogenating an A⋯⋯B single bond and/or halogenating the pyrazole ring in 4-position and/or α-alkylating and/or converting the obtained acid or its salts into one another.

Preferred compounds of the formula IX are pyrazol-1-yl-phenylmethyl derivatives of the formula IX'

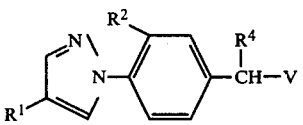

(IX')

wherein R$^1$, R$^2$, R$^4$ and V have their previously-ascribed meanings.

The oxidation of the compounds IX or IX' is effected according to methods known per se. With suitable management of the reaction, oxidation of the V-group and dehydrogenation of the A⋯⋯B single bond are carried out in one step. Suitable processes for the oxidation of V-groups are described for example in Houben-Weyl, Volume 8, pages 384–416. Thus, the reaction is carried out with the most diverse oxidising agents, e.g. with atmospheric oxygen, preferably in the presence of catalysts such as Mn, Co, Fe, Ag, V$_2$O$_5$; with silver oxide, preferably together with copper oxide; with H$_2$O$_2$, preferably in the presence of alkalis; with organic per-acids, such as peracetic acid, per-benzoic acid or per-phthalic acid; with potassium permanganate in aqueous or acetonic solution and/or acid, neutral or alkaline environment, where appropriate with addition of magnesium sulphate; with chromic acid or CrO$_3$, preferably in glacial acetic acid, where appropriate with addition of benzene or sulphuric acid; with nitrous acid; with 2–68% strength nitric acid, where appropriate under pressure (up to 100 atmospheres gauge); with nitric oxides or with caustic alkalis and oxygen in the melt; or with hypohalites.

The oxidation is preferably carried out in inert solvents, such as water, glacial acetic acid, dioxan, benzene, acetone, tetrahydrofuran, dimethyl formamide, ethanol, methanol, or in mixtures of these solvents. The reaction temperatures lie at from −30° C. to 300° C., expediently at room temperature.

The starting compounds of the general formula IX or IX' are obtained according to methods known per se; for example, the aldehydes IX or IX' (V=—CHO) are obtained by reduction of compounds of the formula III, in which F represents an alkoxycarbonyl group, with sodium amalgam or of compounds of the formula III, in which F represents a chlorocarbonyl group, by reduction with hydrogen in the presence of palladium/barium sulphate (Houben-Weyl 7/1 pp. 290–291).

The aldehydes are converted by reduction with sodium borohydrides into the hydroxymethyl derivatives IX or IX' (V=—CH$_2$OH). The hydroxymethyl derivatives IX or IX' are alternatively prepared by direct or catalytic reduction of the compounds III, in which F represents an alkoxycarbonyl group, e.g. by reduction with sodium and ethanol or with lithium hydridoaluminate.

Compounds of formula II (in which R$^4$ is different from hydrogen) are normally obtained in the form of racemic mixtures which, by means of known and conventional processes, are separated into their optically-active isomers. For example, the racemate is converted with an optically-active resolution agent into diastereoisomers which are subsequently separated by selective crystallization and converted into appropriate optical isomers. Illustrative optically-active splitting agents are, e.g., optically-active bases, such as 1- and d-(1-phenyl)ethylamine, cinchonidine or d-ephedrine, from which salts or amides of compounds of formula II are prepared, or optically-active alcohols, such as borneol or menthol, from which esters of compounds of formula II are prepared. Racemic mixtures are also separated by chromatography via optically-active sorbing agents.

PHARMACOLOGY

The distinct antiphlogistic and analgesic effect of the compounds according to the invention can be demonstrated in various tests. As examples, the compounds I to VIII according to the invention were investigated in comparison with commercial compounds (IX) and (X) or compounds (X to XII) described in U.S. Pat. No. 3,896,143. The following Table 1 reproduces the connection between the serial number and the name of the compound investigated.

TABLE 1

| Serial No. | Compound |
|---|---|
| I | 2-[3-chloro-4-(4-chloropyrazol-1-yl)phenyl]-propionic acid |
| II | 4-(4-chloropyrazol-1-yl)phenylacetic acid |
| III | 4-(4-bromopyrazol-1-yl)phenylacetic acid |
| IV | 3-chloro-4-(4-chloropyrazol-1-yl)phenylacetic acid |
| V | 2-[3-chloro-4-(4-bromopyrazol-1-yl)phenyl]acid |
| VI | sodium 2-[2,5-dichloro-4-(pyrazol-1-yl)phenyl]propionate |
| VII | 2-[2,5-dichloro-4-(4-bromopyrazol-1-yl)phenyl]propionic acid |
| VIII | 4-(pyrazol-1-yl)phenylacetic acid |
| IX | phenylbutazone |
| X | indomethacin |
| XI | 4-(1-methyl-5-phenylpyrazol-3-yl)phenylacetic acid |
| XII | 4-(1,5-diphenyl-pyrazol-3-yl)phenylacetic acid |

TABLE 1-continued

| Serial No. | Compound |
|---|---|
| XIII | 4-(1-methyl-5-phenyl-2-pyrazoline-3-yl)phenylacetic acid |

Table 2 reproduces the acute antiphlogistic effect, the toxicity and the therapeutic quotient of the compounds investigated.

TABLE 2

Antiphlogistic effect-measured on the inhibition of carrageenin oedema of rat hind paw after a single oral administration of the substance-and lethal effect-after a single intraperitoneal administration (mouse)

| Substance; serial number | Inhibition of carrageenin oedema of rat hind paw by 40% (=$ED_{40}$) after single oral dose | | Toxicity after single intraperitoneal dose in the mouse $LD_{50}$ mg/kg i.p. |
|---|---|---|---|
| | $ED_{40}$ mg/kg oral | Therapeutic Quotient $LD_{50}/ED_{40}$ | |
| I | 5 | 65 | 325 |
| II | 8 | 58 | 460 |
| III | 4–5 | 122 | 550 |
| IV | 2 | 230 | 460 |
| V | 2 | 163 | 325 |
| VIII | 8 | 150 | 1200 |
| IX | 40 | 6 | 230 |
| X | 4 | 11 | 45 |
| XI | >100* | <4 | 430 |
| XII | 63 | 3 | 200 |
| XIII | >100* | — | — |

*100 mg/kg of the compound cause an oedema inhibition of 25%

The influence of the compounds which were to be tested on carrageenin oedema of rat hind paw was determined as follows:

Female Sprague-Dawley rats (groups of, in each instance, 10 animals; weight of each animal 140–170 g) from which food (Altromin ®R, water ad libitum) is withheld about 16 hours beforehand are each injected subplantarly in the right hind paw with 0.05 ml of a 1% strength carrageenin suspension 1 hour after oral administration of the compounds which are to be tested. The rats are kept at 24° C.

The determination of the paw volume of each rat (in each case, 2–3 individual measurements) is effected plethysmometrically before and 2 and 4 hours after oedema provocation. Each treated group's average percentage paw swelling found at the said times after the carrageenin injection is referred to the paw swelling of the untreated control group (=100%).

As measure for the antiphlogistic effect there serves the average percentage oedema inhibition (i.e. the average from the measured values obtained 3 and 5 hours after administration of the substance).

The determination of the paw volume is effected plethysmometrically. Measuring principle: the liquid volume displaced by the rat paw is registered digitally via an electromechanical pressure converter (Statham P 23 V, 0–200 mm Hg).

The stated doses of the medicaments tested were administered in a liquid volume of 20 ml/kg.

Table 3 and Table 4 reproduce the chronic antiphlogistic effect, the toxicity and the therapeutic quotient of the compounds investigated.

TABLE 3

Antiphlogistic effect-measured on the inhibition of granulation tissue formation (rat; 7-day treatment) - and lethal effect (mouse; $LD_{50}$ after intraperitoneal administration)

| Substance; serial number | Inhibition of granulation tissue formation after subcutaneous cotton-wool implantation by 20% (=$ED_{20}$) in the rat after 7-day oral administration | | Lethal effect $LD_{50}$ after single intraperitoneal administration to the mouse mg/kg i.p. |
|---|---|---|---|
| | $ED_{20}$ mg/kg/die | Therapeutic Quotient $LD_{50}/ED_{20}$ | |
| I | 3 | 108.3 | 325 |
| IV | 20 | 23.0 | 460 |
| V | ~10 | ~32.5 | 325 |
| IX | 100 | 2.3 | 230 |
| X | 3–5 | 12.8 | 45 |

Test procedure for the investigation of the influence of the compounds which are to be tested on granulation tissue formation after cotton-wool implantation in the rat (so-called cotton pellet method):

Male Sprague-Dawley rats (in each instance, groups of 8 animals; weight of each animal 150–170 g) in ether anaesthesia and under sterile conditions are each implanted subcutaneously on both sides of the shoulder-blade region with 1 cotton-wool pellet (manufacturer: the firm of Hartmann/Heidenheim; cotton-wool pellet, size 2, No. 4865/2) of 13.0±0.5 mg which beforehand was soaked with 0.1 ml of a solution of 0.5 mg penicillin G and 0.8 streptomycin sulphate/1 ml distilled water. Closure of the skin cut is effected by means of clips.

On seven consecutive days the compounds which are to be tested (as sodium salt in aqueous solution) or the corresponding amount (5 ml/kg/day) of tap water (=control group) are administered orally daily.

On the eighth day the animals are killed, the cotton-wool granulomata are cautiously freed without cutting, i.e. preserving the fibrous capsule, dried (15 hours at 120° C.) and weighed. By deducting the weight component of the cotton-wool pellets the amount of newly formed granulation tissue is obtained.

As measure for the anti-proliferative effect of a compound there serves the percentage lessening of the average granuloma dry weight of a treated group (=16 granulomata) compared to the control group (=100%).

TABLE 4

Anti-arthritic effect (so-called adjuvant arthritis; rat; $ED_{25}$; 5-day oral administration) and acute toxicity ($LD_{50}$ after single intraperitoneal administration; mouse)

| Substance; serial number | Inhibition of adjuvant arthritis by 25% (=$ED_{25}$) in the rat after a 5-day oral application | | $LD_{50}$ after a single administration mouse mg/kg i.p. |
|---|---|---|---|
| | $ED_{50}$ mg/kg/die p.o. | Therapeutic Quotient $LD_{50}/ED_{25}$ | |
| I | 0.2 | 1625 | 325 |

TABLE 4-continued

Anti-arthritic effect (so-called adjuvant arthritis; rat; $ED_{25}$; 5-day oral administration) and acute toxicity ($LD_{50}$ after single intraperitoneal administration; mouse)

Inhibition of adjuvant arthritis

| Substance; serial number | by 25% ($=ED_{25}$) in the rat after a 5-day oral application | | $LD_{50}$ after a single administration mouse mg/kg i.p. |
|---|---|---|---|
| | $ED_{50}$ mg/kg/die p.o. | Therapeutic Quotient $LD_{50}/ED_{25}$ | |
| IV | 0.7 | 657 | 460 |
| V | 0.2 | 1625 | 325 |
| IX | 3 | 77 | 230 |
| X | 0.1 | 450 | 45 |

The influence of the compounds which are to be tested on rat polyarthritis caused by Mycobacterium butyricum (so-called "adjuvant arthritis") was determined with the experimental arrangement described in the following:

In imitation of the method described by NEWBOULD and PERRINE et al. [NEWBOULD, B. B.; Brit. J. Pharmacol. 21, 127 (1963); PERRINE, J. W. and TAKESUE, E. I.; Arch. int. Pharmacodyn. 174, 192–198 (1968)] there is induced in rats, through intradermal injection of a Myobact. butyricum/paraffin oil suspension into the tail root, a so-called adjuvant arthritis which manifests itself especially in a strong swelling of the tail (primary lesion) and the paws (secondary lesion). Antiphlogistic agents inhibit this swelling reaction.

Male Sprague-Dawley rats (150–190 g) are each injected intradermally into the tail root on day zero with 0.1 ml/animal of a 0.5% strength Myobact. butyrum/paraffin oil suspension. The first paw volume determination is effected on the day before the administration of the adjuvant; in the ensuing 2 to 3 weeks the paw volume then increases by about 80% (=so-called secondary lesion). On the 17th day after administration of adjuvant, all positively-reacting animals (paw volume increase at least 30%) are selected and concentrated in groups of 10 animals with equal paw volume distribution.

The compounds to be tested are now administered on the following 5 days, that is to say from the 17th to the 21st day after administration of adjuvant, once daily orally in 10 ml/kg of liquid.

As measure for the anti-arthritic effect there serves the decrease of the paw swelling on the 21st day after the administration of adjuvant, referred in each case to the paw swelling of the control group (=100%); the paw volume is determined plethysmometrically.

Table 5 reproduces the analgesic effect, the toxicity and the therapeutic quotient of the compounds investigated.

TABLE 5

Analgesic effect - measured on the influence on the pain reaction provoked in the rat through bending of an inflamed ankle joint ($AgNO_3$ inflammation) - and acute toxic effect (intraperitoneal administration; mouse)

| Substance; serial number | Analgesic effect $ED_{25}$ (= dose which in 25% of the animals completely suppresses the pain reaction) mg/kg oral | Therap. Quotient $LD_{50}/ED_{25}$ | Toxicity after single intraperitoneal administration to the mouse $LD_{50}$ mg/kg i.p. |
|---|---|---|---|
| I | 0.4 | 813 | 325 |
| III | 1.2 | 458 | 550 |
| IV | 2.5 | 184 | 460 |
| V | 0.8 | 406 | 325 |
| VI | 2.5 | 420 | 1050 |
| VII | 1.2 | 238 | 285 |
| IX | 2 | 115 | 230 |
| X | 0.3 | 150 | 45 |

The influence of the compounds which were to be tested on the pain reaction provoked in the rat through bending of an inflamed tarsal joint ($AgNO_3$ inflammation) was determined as follows:

In imitation of HOFFMEISTER et al [Arzneim.-Forsch. 24 (1974) 600] female Sprague-Dawley rats (each animal about 200 g) under ether anaesthesia are injected in the right hind paw ankle joint (inside) with 0.2 ml of a 1% strength silver nitrate solution. The animals are kept at 24° C. and receive as food Altromin ®R and water ad libitum. After the $AgNO_3$ injection a scream reaction can be induced in nearly all the animals (90–95%) through moderate bending of the ankle joint. All the positively-reacting animals are concentrated in groups of 10 animals. The compounds which are to be tested are administered orally in a liquid volume of 20 ml/kg 1 hour before the $AgNO_3$ application; the untreated control animals receive the corresponding amount of tap water.

Within 5 hours after administration of the substance the number of reacting animals is ascertained at hourly intervals.

As measure for the analgesic effect there serves the maximum % proportion of the protected animals within 5 hours after administration of the substance [referred to the number of reacting animals of the control group (=100%)]

TABLE 6

Antipyretic effect - measured on the influence of the compounds which are to be tested on the yeast fever of the rat (oral administration of the substance) - and acute toxicity (intraperitoneal administration; mouse)

| Substance; serial number | Antipyretic effect $ED_{0.75}$* mg/kg oral | Therapeutic Quotient $ED_{50}/ED_{0.75}$ | Toxicity after single intraperitoneal administration in the mouse $LD_{50}$ mg/kg i.p. |
|---|---|---|---|
| I | 3.5 | 92.9 | 325 |
| III | 20 | 27.5 | 550 |
| V | 5 | 65 | 325 |
| VIII | 32 | 37.5 | 1200 |
| IX | 15 | 15.3 | 230 |
| X | 2.5 | 18 | 45 |

*$ED_{0.75}$ = dose which lowers the yeast fever of the rat by 0.75° C.

The antipyretic effect is determined from the influence of the compounds to be tested on the yeast fever of the rat.

In female Sprague-Dawley rats (in each series of experiments, 30 rats in groups of 5 animals; animal weight 170–200 g) a hyperthermia is produced through subcutaneous injection (neck) of 20 ml/kg of a 20% strength aqueous brewer's yeast suspension (brewers' yeast "Heliosan"/Hefereformwerk Radolfzell). 24 hours after the yeast injection, the body temperature is measured rectally at hourly intervals.

After a preliminary measurement the compounds which are to be tested are administered to the animals orally in a liquid volume of 5 ml/kg; a control group receives the corresponding amount of tap water. Food (Altromin®R, water ad libitum) was withheld from the rats 18 hours beforehand. The rats are kept at about 23° C.

As measure for the antipyretic effect there serves the maximum lowering of temperature (with reference to the temperature of the preliminary measurement, i.e. immediately before administration of the substance) in the course of 4 hours. The body temperature is measured with a Iastomed H (Braun electronic).

From the preceding data of Tables 2–6 there is seen the superiority of the compounds according to the invention over those of the prior art.

The following examples illustrate the invention in more detail without restricting it. The stated temperatures are given in °C. The abbreviation "m.p." denotes melting point; the abbreviation "b.p." denotes boiling point.

EXAMPLE 1

20 g (100 mmoles) of 2-(4-amino-3-chlorophenyl)propionic acid are dissolved in 20 ml of concentrated hydrochloric acid and diazotized with 6.9 g of sodium nitrite in 20 ml of water at from −2° to −6° C. The solution is thereafter stirred for a further hour and subsequently stirred into 100 ml of a freshly-prepared, ice-cold, 5.5 N solution of sodium hydrogen sulfite. Heating is then effected slowly to a temperature of from 60° to 70° C. After one hour, acidification is effected with concentrated hydrochloric acid, and the resulting reaction mixture is left at 70° C. for a further 12 hours. 2-(3-chloro-4-hydrazinophenyl)propionic acid forms therein. 22 g (100 mmoles) of 1,1,3,3-tetraethoxypropane are then added thereto. After three hours' heating to 100° C., the reaction mixture is cooled, rendered alkaline with 35% strength sodium hydroxide solution and, in order to saponify the 2-[3-chloro-4-(pyrazol-1-yl)phenyl]propionic acid ethyl ester which is formed in addition to the acid, reheated for one hour. After cooling, impurities are extracted by shaking with benzene; the aqueous phase is acidified with concentrated hydrochloric acid; the product is extracted with diethyl ether; and the ether phase is washed with water, dried and concentrated in a vacuum. 24 g (96% of theory) of 2-[3-chloro-4-(pyrazol-1-yl)phenyl]propionic acid, m.p. 83° to 85° C., are thus obtained.

Analogously, diazotization and reduction of each of:
2-(4-aminophenyl)propionic acid,
4-aminophenylacetic acid,
4-amino-3-chlorophenylacetic acid,
4-amino-3-bromophenylacetic acid,
4-amino-3,5-dichlorophenylacetic acid,
2-aminophenylacetic acid and
2-(4-amino-2,5-dichlorophenyl)propionic acid
4-amino-mandelic acid (=4-amino-α-hydroxyphenylacetic acid)
3-amino-2,6-dichlorophenylacetic acid result in the preparation of
2-(4-hydrazinophenyl)propionic acid,
4-hydrazinophenylacetic acid,
3-chloro-4-hydrazinophenylacetic acid,
3-bromo-4-hydrazinophenylacetic acid,
3,5-dichloro-4-hydrazinophenylacetic acid,
2-hydrazinophenylacetic acid and
2-(2,5-dichloro-4-hydrazinophenyl)propionic acid,
4-hydrazinomandelic acid
2,6-dichloro-3-hydrazinophenylacetic acid, respectively, and, further by subsequent reaction with 1,1,3,3-tetraethoxypropane,
2-[4-(pyrazol-1-yl)phenyl]propionic acid (m.p. 137° to 138° C.),
4-(pyrazol-1-yl)phenylacetic acid (m.p. 138° to 139° C.),
3-chloro-4-(pyrazol-1-yl)phenylacetic acid (oil),
3-bromo-4-(pyrazol-1-yl)phenylacetic acid (m.p. 100° to 101° C.)
3,5-dichloro-4-(pyrazol-1-yl)phenylacetic acid (m.p. 196° to 198° C.),
2-(pyrazol-1-yl)phenylacetic acid (m.p. 96° to 97° C.) and
2-[2,5-dichloro-4-(pyrazol-1-yl)phenyl]propionic acid (oil),
4-(pyrazol-1-yl)mandelic acid,
2,6-dichloro-3-(pyrazol-1-yl)phenylacetic acid (oil), respectively.

EXAMPLE 2

(a) 31 g (92 mmoles) of 4-hydraziniumphenylacetic acid p-toluenesulfonate, 8.2 g (100 mmoles) of sodium acetate, 25 ml (104 mmoles) of 1,1,3,3-tetraethoxypropane and 150 ml of glacial acetic acid are heated to 100° C. for 2 hours. Subsequently, the solvent is distilled off, 2 N NaOH is added to the residue, and the resulting alkaline solution is extracted with benzene. The aqueous phase is clarified with activated charcoal and acidified with concentrated hydrochloric acid (with ice cooling); the precipitate is suction filtered and washed with water to produce 15.8 g (85% of theory) of 4-(pyrazol-1-yl)phenylacetic acid, m.p. 138° to 139° C.

Analogously, each of
2-(4-hydraziniumphenyl)propionic acid p-toluenesulfonate,
2-(3-chloro-4-hydraziniumphenyl)propionic acid p-toluenesulfonate and
3-chloro-4-hydraziniumphenylacetic acid p-toluenesulfonate
is separately reacted with
1,1,3,3-tetraethoxypropane or tetramethoxypropane, to produce
2-[4-(pyrazol-1-yl)phenyl]propionic acid (m.p. 137° to 138° C.),
2-[3-chloro-4-(pyrazol-1-yl)phenyl]propionic acid (m.p. 83° to 85° C.) and
3-chloro-4-(pyrazol-1-yl)phenylacetic acid (oil), respectively.

(b) The starting compound is obtained in the following manner: 16.5 g of 2-(4-aminophenyl)propionic acid (0.1 mole) are dissolved in 60 ml of concentrated hydrochloric acid and 40 ml of water and diazotized with a solution of 6.9 g of sodium nitrite (0.1 mole) in 30 ml of water at −4° C. The resulting reaction mixture is thereafter stirred for a further 2 hours at 0°, then stirred into a solution of 68 g (0.3 mmole) of tin(II) chloride at 0° to 2° C. and left to stand for 12 hours. With 20 g of p-toluenesulfonic acid, 2-(4-hydrazinophenyl)propionic acid is precipitated as a salt. The voluminous precipitate is suction filtered and dried over potassium hydroxide to produce 32 g (91% of theory) of 2-(4-hydraziniumphenyl)propionic acid p-toluenesulfonate, m.p. 234° to 235° C.

Analogously, from each of
4-aminophenylacetic acid,
3-chloro-4-aminophenylacetic acid and
2-(3-chloro-4-aminophenyl)propionic acid there are obtained, by diazotization, reaction with tin(II) chloride and precipitation with p-toluenesulfonic acid,
4-hydraziniumphenylacetic acid p-toluenesulfonate (m.p. 225° to 227° C., with decomposition),
3-chloro-4-hydraziniumphenylacetic acid p-toluenesulfonate (m.p. 201° to 202° C., with decomposition) and
2-(3-chloro-4-hydraziniumphenyl)propionic acid p-toluenesulfonate (m.p. 188° to 189° C.), respectively.

EXAMPLE 3

16.6 g (100 mmoles) of 2-hydrazinophenylacetic acid are stirred with 29.3 g (100 mmoles) of chloromalondialdehydedianil hydrochloride in 400 ml of 6 N hydrochloric acid at 100° C. for two hours. Subsequently, extraction is effected with chloroform. The chloroform phase is subsequently extracted with 2 N solution of sodium hydroxide, and then the aqueous phase is acidified with hydrochloric acid. Extraction is again effected with chloroform; the latter chloroform extract is dried, and solvent is subsequently removed therefrom by evaporation; 2-(4-chloropyrazol-1-yl)phenylacetic acid remains behind as oil. By neutralization with sodium hydroxide solution, concentration, and rubbing (spreading over, triturating) with diethyl ether, the sodium salt (recrystallized from ethanol, m.p. 245° to 247° C.) is obtained.

Analogously, 2-(3-chloro-4-hydrazinophenyl)propionic acid (by reaction with chloromalondialdehydedianil hydrochloride, chloromalondialdehydemonoanil or chloromalondialdehyde) yields 2-[3-chloro-4-(4-chloropyrazol-1-yl)phenyl]propionic acid (m.p. 102° to 103° C.) or (by reaction with bromomalondialdehydedianil dihydrobromide, bromomalondialdehydemonoanil or bromomalondialdehyde) 2-[3-chloro-4-(4-bromopyrazol-1-yl)phenyl]propionic acid (m.p. 116° to 117° C.).

EXAMPLE 4

13.5 g (38 mmoles) of 2-(4-hydraziniumphenyl)propionic acid p-toluenesulfonate, 7.85 g of sodium acetate and 10 g (38 mmoles) of 1-dimethylamino-3-dimethylimmonio-2-chloropropene perchlorate are dissolved in 100 ml of glacial acetic acid, stirred for one hour at room temperature and subsequently for 3 hours at 100° C. After the glacial acetic acid is distilled off, 300 ml of chloroform are added to the resulting residue; the organic phase is washed with water, dried, clarified with Tonsil ® and concentrated to yield 6.6 g (69% of theory) of 2-[4-(4-chloropyrazol-1-yl)phenyl]propionic acid, m.p. 152° to 153° C.

Analogously, 2-[3-chloro-4-(chloropyrazol-1-yl)phenyl]propionic acid is obtained by reaction of 2-[3-chloro-4-hydraziniumphenyl]propionic acid p-toluenesulfonate with 1-dimethylamino-3-dimethylimminio-2-chloropropene perchlorate.

Analogously, 4-(4-chloropyrazol-1-yl)mandelic acid is obtained by reaction of 4-hydraziniummandelic acid chloride with 1-dimethylamino-3-dimethylimminio-2-chloropropene perchlorate.

EXAMPLE 5

25 g (100 mmoles) of 2-[3-chloro-4-(pyrazol-1-yl)phenyl]propionic acid are dissolved in 250 ml of chloroform. Chlorine is introduced (2 l/h) into the resulting solution (reaction mixture) at room temperature, with vigorous stirring, until a precipitate begins to separate (after about 2 hours). After about a further half hour, the introduction of chlorine is stopped; the endpoint of the chlorination is ascertained through the disappearance of the starting product in a thin-layer chromatogram ($CHCl_3$/benzene/glacial acetic acid 10/10/1; silica gel). 250 ml of methylene chloride are added to the reaction mixture, and excess chlorine is removed by washing with sodium hydrogen sulfite solution and subsequently with water. The organic phase is dried and concentrated; the residue is brought to crystallization through rubbing with carbon tetrachloride.

28 g (98% of theory) of 2-[3-chloro-4-(4-chloropyrazol-1-yl)phenyl]propionic acid, m.p. 102° to 103° C. (from $CCl_4$) are obtained.

Analogously, reacting each of:
2-[4-(pyrazol-1-yl)phenyl]propionic acid,
4-(pyrazol-1-yl)phenylacetic acid,
3-chloro-4-(pyrazol-1-yl)phenylacetic acid),
2-(pyrazol-1-yl)phenylacetic acid,
3-bromo-4-(pyrazol-1-yl)phenylacetic acid, and
2-[3-bromo-4-(pyrazol-1-yl)phenyl]propionic acid with chlorine yields
2-[4-(4-chloropyrazol-1-yl)phenyl]propionic acid (m.p. 152° to 153° C.),
4-(4-chloropyrazol-1-yl)phenylacetic acid (m.p. 176° to 178° C.),
3-chloro-4-(4-chloropyrazol-1-yl)phenylacetic acid (m.p. 132° to 133° C.),
2-(4-chloropyrazol-1-yl)phenylacetic acid (oil; sodium salt m.p. 245° to 247° C.),
3-bromo-4-(4-chloropyrazol-1-yl)phenylacetic acid (m.p. 138° to 139° C.) and
2-[3-bromo-4-(4-chloropyrazol-1-yl)phenyl]propionic acid (m.p. 124° C.), respectively.

EXAMPLE 6

20.2 g (100 mmoles) of 4-(pyrazol-1-yl)phenylacetic acid are dissolved in 400 ml of carbon tetrachloride. 16 g of bromine (200 mmoles) in 400 ml of carbon tetrachloride are added dropwise, with ice cooling, to the resulting solution. After subsequent stirring for half an hour at room temperature, washing with sodium dithionite solution is effected; this is followed by drying with sodium sulfate and, finally, by evaporation to dryness to obtain 27.5 g (98% of theory) of 4-(4-bromo-pyrazol-1-yl)phenylacetic acid, m.p. 187° C. (from acetonitrile).

Analogously, reaction of each of
2-[3-chloro-4-(pyrazol-1-yl)phenyl]propionic acid,
2-[4-(pyrazol-1-yl)phenyl]propionic acid,
3-chloro-4-(pyrazol-1-yl)phenylacetic acid,
2-[2,5-dichloro-4-(pyrazol-1-yl)phenyl]propionic acid,
3-bromo-4-(pyrazol-1-yl)phenylacetic acid and
2-[3-bromo-4-(pyrazol-1-yl)phenyl]propionic acid with bromine yields
2-[3-chloro-4-(4-bromopyrazol-1-yl)phenyl]propionic acid (m.p. 116° to 117° C.), 2-[4-(4-bromopyrazol-1-yl)phenyl]propionic acid,
3-chloro-4-(4-bromopyrazol-1-yl)phenylacetic acid (m.p. 160° to 161° C.),
2-[2,5-dichloro-4-(4-bromopyrazol-1-yl)phenyl]propionic acid (m.p. 188° C.),
3-bromo-4-(4-bromopyrazol-1-yl)phenylacetic acid (m.p. 155° to 159° C.) and
2-[3-bromo-4-(4-bromopyrazol-1-yl)phenyl]propionic acid (m.p. 115° to 116° C.), respectively.

EXAMPLE 7

2.5 g (10 mmoles) of 2-[3-chloro-4-(pyrazol-1-yl)phenyl]propionic acid are dissolved in 30 ml of methylene chloride. A solution of 2.01 g (15 mmoles) of sulfuryl chloride in 10 ml of chloroform is added dropwise, with cooling to the resulting solution; heating is effected gradually to room temperature; and this is followed by boiling under reflux for 2 hours. The reaction solution is allowed to cool; the solvent is distilled off; 50 ml of 2 N solution of sodium hydroxide are added to the thus-obtained residue, and boiling up is effected for a few minutes. The reaction solution is extracted with diethyl ether and then acidified with hydrochloric acid. After renewed extraction with diethyl ether, the combined ether phases are dried and evaporated to produce 2.6 g (90% of theory) of 2-[3-chloro-4-(4-chloropyrazol-1-yl)phenyl]propionic acid, m.p. 102° to 103° C.

Analogously, reaction of each of
2-[4-(pyrazol-1-yl)phenyl]propionic acid,
4-(pyrazol-1-yl)phenylacetic acid,
3-chloro-4-(pyrazol-1-yl)phenylacetic acid,
2-(pyrazol-1-yl)phenylacetic acid,
2-[3-chloro-4-(pyrazol-1-yl)phenyl]butyric acid and
2-[2,5-dichloro-4-(pyrazol-1-yl)phenyl]propionic acid
with sulfuryl chloride yields
2-[4-(4-chloropyrazol-1-yl)phenyl]propionic acid (m.p. 152° to 153° C.),
4-(4-chloropyrazol-1-yl)phenylacetic acid (m.p. 176° to 178° C.),
3-chloro-4-(4-chloropyrazol-1-yl)phenylacetic acid (m.p. 132° to 133° C.),
2-(4-chloropyrazol-1-yl)phenylacetic acid (oil),
2-[3-chloro-4-(4-chloropyrazol-1-yl)phenyl]butyric acid (m.p. 103° to 104° C.) and
2-[2,5-dichloro-4-(4-chloropyrazol-1-yl)phenyl]propionic acid (m.p. 168° to 169° C.), respectively.

EXAMPLE 8

11.85 g (35 mmoles) of 4-hydraziniumphenylacetic acid p-toluenesulfonate and 4.5 g (40 mmoles) of fluoromalondialdehyde sodium salt are stirred into a mixture of 140 ml of concentrated hydrochloric acid and 140 ml of ethanol. After 12 hours' stirring at room temperature followed by 30 minutes' heating to 80° C., a further 300 ml of ethanol and 900 ml of benzene are added. For complete esterification of the intermediately-formed 4-(4-fluoropyrazol-1-yl)phenylacetic acid, the water is removed as azeotrope with a water separator. The organic solution is extracted with soda solution; the solvent is distilled off in a vacuum; and the resulting residue is chromatographed with chloroform-ethyl acetate on silica gel to produce 5.2 g (52% of theory) of crystalline 4-(4-fluoropyrazol-1-yl)phenylacetic acid ethyl ester (m.p. 83.5° to 84.5° C.).

Analogously, 3-chloro-4-(4-fluoropyrazol-1-yl)phenylacetic acid ethyl ester (b.p. 115° to 118° C./$2.10^{-2}$ mm Hg) is obtained in a 65% yield by reacting 3-chloro-4-hydraziniumphenylacetic acid p-toluenesulfonate and the sodium salt of fluoromalondialdehyde.

EXAMPLE 9

20 g (0.1 mole) of 4-hydraziniumphenylacetic acid chloride and 22 g (0.1 mole) of B 1,1,3,3-tetraethoxypropane are heated under reflux for 2 hours in 250 ml of absolute ethanol (saturated with hydrogen chloride). After the solvent is distilled off, the residue is taken up in benzene; the organic solution is then washed with 2 N soda solution and with water, dried and concentrated in a vacuum; and the resulting residue is recrystallized from cyclohexane to yield 16 g (69% of theory) of 4-(pyrazol-1-yl)phenylacetic acid ethyl ester, m.p. 49° C.

Analogously, 4-(pyrazol-1-yl)phenylacetic acid ethyl ester is obtained from 4-hydraziniumphenylacetic acid ethyl ester chloride.

EXAMPLE 10

4.4 g (17.7 mmoles) of 4-(4-fluoropyrazol-1-yl)phenylacetic acid ethyl ester in 60 ml of 1 N solution of sodium hydroxide are heated to 100° C. for 2 hours. After cooling and extraction with benzene, clarification (effected with activated charcoal) is followed by acidification with concentrated hydrochloric acid to produce 3.7 g (95% of theory) of 4-(4-fluoropyrazol-1-yl)phenylacetic acid, m.p. 165° to 167° C. (from acetonitrile).

Analogously, 3-chloro-4-(4-fluoropyrazol-1-yl)phenylacetic acid (m.p. 110° to 112.5° C.) and 4-(pyrazol-1-yl)phenylacetic acid (m.p. 138° to 139° C.) and 4-(4-chloropyrazol-B 1-yl)phenylglyoxylic acid (m.p. 113° to 116° C.) are obtained by saponification of the corresponding ethyl esters.

EXAMPLE 11

5 g (17.5 mmoles) of 2-[3-chloro-4-(4-chloropyrazol-1-yl)phenyl]propionic acid are dissolved in 17.5 ml of 1 N sodium hydrogen carbonate solution. 11.8 ml (17.5 mmoles) of a 1.5 molar calcium chloride solution are added to the resulting salt solution, with stirring. During heating on a water bath, a voluminous precipitate of the calcium salt is formed. After suction filtration, the calcium salt, m.p. about 190° C. (sintering from 155° C.), is recrystallized from water/ethanol (1:1).

The calcium salt of 3-chloro-4-(pyrazol-1-yl)phenylacetic acid (sintering from 175° C.) and the calcium salt of 2,6-dichloro-3-(pyrazol-1-yl)phenylacetic acid (sintering from 200° C. to 250° C.) are analogously prepared.

Analogously, 2-[3-chloro-4-(4-chloropyrazol-1-yl)phenyl]propionic acid and copper(II) chloride yield copper(II)-2-[3-chloro-4-(4-chloropyrazol-1-yl)phenyl]propionate (m.p. 230° C.).

EXAMPLE 12

5 g (17.5 mmoles) of 2-[3-chloro-4-(4-chloropyrazol-1-yl)phenyl]propionic acid together with 2.6 g (17.5 mmoles) of triethanolamine are dissolved in 30 ml of chloroform; the solution is extracted with 20 ml of water. After the water is evaporated off, the resulting residue is taken up in ethanol and crystallized in a crystallizing dish. The triethanolamine salt (m.p. 108° to 111° C.) is recrystallized from acetonitrile/diethyl ether.

The following salts of 2-[3-chloro-4-(4-chloropyrazol-1-yl)phenyl]propionic acid are analogously prepared:

cinchonidinium-2-[3-chloro-4-(4-chloropyrazol-1-yl)phenyl]propionate (m.p. 144° to 146° C.), D-1-phenylethylammonium-2-[3-chloro-4-(4-chloropyrazol-1-yl)phenyl]propionate (m.p. 167° to 168° C.), L-1-phenylethylammonium-2-[3-chloro-4-(4-chloropyrazol-1-yl)phenyl]propionate (m.p. 167° to 168° C.), (L)-lysine-2-[3-chloro-4-(4-chloropyrazol-1-yl)phenyl]-propionate (m.p. 176° to 180° C.) and piperazine-bis-{2-[3-chloro-4-(4-chloropyrazol-1-yl)phenyl]propionate} (m.p. 96° to 98° C.).

EXAMPLE 13

(a) 2.3 g (10 mmoles) of 4-(pyrazol-1-yl)phenylacetic acid ethyl ester are dissolved in 20 ml of dimethylformamide; 240 mg (10 mmoles) of sodium hydride are added, under nitrogen, with good cooling (ice, sodium chloride) and vigorous stirring is effected until hydrogen evolution subsides. A solution of 1.5 g of methyl iodide and 5 ml of dimethyl formamide is then added dropwise, and stirring at room temperature is subsequently effected over night. The reaction mixture is poured onto water and extracted with diethyl ether. The ethereal solution is concentrated to yield 2-[4-(pyrazol-1-yl)phenyl]propionic acid ethyl ester as oil.

Analogously, reaction of 3-chloro-4-(4-chloropyrazol-1-yl)phenylacetic acid methyl ester, 3-chloro-4-(pyrazol-1-yl)phenylacetic acid ethyl ester, 3-chloro-4-(4-bromopyrazol-1-yl)phenylacetic acid ethyl ester or 3-bromo-4-(pyrazol-1-yl)phenylacetic acid ethyl ester with methyl iodide yields 2-[3-chloro-4-(4-chloropyrazol-1-yl)phenyl]propionic acid methyl ester (b.p. 134° to 135° C./0.03 mm Hg), 2-[3-chloro-4-(pyrazol-1-yl)phenyl]propionic acid ethyl ester (b.p. 120° C./10$^{-2}$ mm Hg), 2-[3-chloro-4-(4-bromopyrazol-1-yl)phenyl]propionic acid ethyl ester or 2-[3-bromo-4-(pyrazol-1-yl)phenyl]propionic acid ethyl ester (b.p. 130° C./10$^{-2}$ mm Hg), respectively.

Similarly, reaction of 3-chloro-4-(pyrazol-1-yl)phenylacetic acid ethyl ester with ethyl iodide yields 2-[3-chloro-4-(pyrazol-1-yl)phenyl]butyric acid ethyl ester (b.p. 140° C./0.01 mm Hg).

(b) The crude 2-[4-(pyrazol-1-yl)phenyl]propionic acid ethyl ester from (a) is boiled for 3 hours with 50 ml of 1 N solution of sodium hydroxide, and the thus-obtained solution is extracted with benzene. The aqueous phase is acidified with hydrochloric acid and extracted with benzene. The organic phase is then dried and concentrated; the residue is recrystallized from benzene/cyclohexane (1:1) to yield 1.7 g (80% of theory) of 2-[4-(pyrazol-1-yl)phenyl]propionic acid, m.p. 137° to 138° C.

EXAMPLE 14

3.0 g (10 mmoles) of 2-[3-chloro-4-(4-chloropyrazol-1-yl)phenyl]propionic acid methyl ester, 1.4 g of potassium hydroxide, 1.5 ml of water and 20 ml of ethanol are heated to the boil for 2 hours, the alcohol is distilled off, water is added and extraction with benzene is effected. This is followed by clarification of the aqueous phase with activated charcoal and acification with 2 N hydrochloric acid to produce 2.7 g (95% of theory) of 2-[3-chloro-4-(4-chloropyrazol-1-yl)-phenyl]propionic acid (m.p. 102° to 103° C.).

Analogously, saponification of each of:

2-[3-chloro-4-(pyrazol-1-yl)phenyl]propionic acid ethyl ester,

2-[3-chloro-4-(4-bromopyrazol-1-yl)phenyl]propionic acid ethyl ester,

2-[3-chloro-4-(4-chloropyrazol-1-yl)phenyl]propionic acid butyl ester,

2-[3-chloro-4-(4-chloropyrazol-1-yl)phenyl]propionic acid benzyl ester,

2-[3-chloro-4-(pyrazol-1-yl)phenyl]butyric acid ethyl ester, 3-bromo-4-(pyrazol-1-yl)phenylacetic acid ethyl ester, 4-(4-chloropyrazol-1-yl)phenylacetic acid ethyl ester and 2-[3-bromo-4-(pyrazol-1-yl)phenyl]propionic acid ethyl ester yields 2-[3-chloro-4-(pyrazol-1-yl)phenyl]propionic acid (m.p. 83° to 85° C.), 2-[3-chloro-4-(4-bromopyrazol-1-yl)phenyl]propionic acid (m.p. 116° to 117° C.), 2-[3-chloro-4-(4-chloropyrazol-1-yl)phenyl]propionic acid (m.p. 102° to 103° C.), 2-[3-chloro-4-(pyrazol-1-yl)phenyl]butyric acid (m.p. 77° to 79° C.), 3-bromo-4-(pyrazol-1-yl)phenylacetic acid (m.p. 100° to 101° C.), 4-(4-chloropyrazol-1-yl)phenylacetic acid (m.p. 176° to 178° C.) and 2-[3-bromo-4-(pyrazol-1-yl)phenyl]propionic acid (viscous oil), respectively.

EXAMPLE 15

2.15 g (8.5 mmoles) of 2-chloro-4-(4-chloropyrazol-1-yl)phenylacetonitrile and 14 g of 63 percent strength sulfuric acid are stirred for 6 hours at 105° C., and the resulting mixture is then poured onto 90 g of ice. Stirring is effected for 10 minutes, followed by suction filtration and washing with water to obtain 2.3 g (99.5% of theory) of 2-chloro-4-(4-chloropyrazol-1-yl)phenylacetic acid (m.p. 152.5° to 153° C.).

Analogously, hydrolysis of 3-chloro-4-(4-chloropyrazol-1-yl)phenylacetonotrile with sulfuric acid yields 3-chloro-4-(4-chloropyrazol-1-yl)phenylacetic acid (m.p. 132° to 133° C.).

The starting compounds are obtained in the following manner:

(a) 41.0 g (186 mmoles) of 1,1,3,3-tetraethoxypropane are added dropwise at 40° C. to 30 g (155 mmoles) of 3-chloro-p-tolylhydrazine hydrochloride in 180 ml of methanol and 15.6 ml of concentrated hydrochloric acid and heated to the boil for 1.5 hours. The resulting solution is concentrated in a vacuum; the thus-prepared concentrate is dissolved in benzene. The obtained benzene solution is washed with water and sodium hydrogen carbonate solution, dried and evaporated to dryness to yield 26 g (87% of theory) of 1-(3-chloro-p-tolyl)pyrazole (m.p. 61° to 62° C.).

Analogously, 1-(2-chloro-p-tolyl)pyrazole and 1-(2-bromo-p-tolyl)pyrazole are obtained [from 2-chloro-p-tolylhydrazine and 2-bromo-p-tolylhydrazine, respectively, and 1,1,3,3-tetraethoxypropane].

(b) A cooled solution of 8 g (113 mmoles) of chlorine in 50 ml of chloroform is added dropwise at 0° C. to a solution of 19.8 g (103 mmoles) of 1-(3-chloro-p-tolyl)pyrazole in 100 ml of chloroform, and stirring is effected for a further 2 hours at from 3° to 8° C. The organic phase is washed with water and dilute sodium dithionite solution; drying is effected, followed by concentration to dryness to produce 21.2 g (91% of theory) of 4-chloro-1-(3-chloro-p-tolyl)pyrazole (m.p. 69° to 70° C.).

Analogously, 4-bromo-1-(3-chloro-p-tolyl)pyrazole [from 1-(3-chloro-p-tolyl)pyrazole and bromine], 4-chloro-1-(2-chloro-p-tolyl)pyrazole [from 1-(2-chloro-p-tolyl)pyrazole and chlorine], 4-bromo-1-(2-bromo-p-tolyl)pyrazole [from 1-(2-bromo-p-tolyl)pyrazole and bromine], 4-bromo-1-(2-chloro-p-tolyl)pyrazole [from 1-(2-chloro-p-tolyl)pyrazole and bromine] and 4-chloro-1-(2-bromo-p-tolyl)pyrazole [from 1-(2-bromo-p-tolyl)pyrazole and chlorine] are obtained.

(c) 16 g of 4-chloro-1-(3-chloro-p-tolyl)pyrazole, 13 g of N-bromosuccinimide, 0.32 g of dibenzoylperoxide and 170 ml of carbon tetrachloride are heated to the boil for 1.5 hours. The resulting solution is cooled, filtered and evaporated to dryness. The obtained residue (20.1 g) is recrystallized from cyclohexane to yield 14.7 g (68% of theory) of 4-chloro-1-(4-bromomethyl-3-chlorophenyl)pyrazole (m.p. 77° to 78° C.).

Analogously, bromation with N-bromosuccinimide of the pyrazoles described under (b) yields 4-bromo-1-(4-bromomethyl-3-chlorophenyl)pyrazole,
4-chloro-1-(4-bromomethyl-2-chlorophenyl)pyrazole,
4-bromo-1-(4-bromomethyl-2-bromophenyl)pyrazole,
4-bromo-1-(4-bromomethyl-2-chlorophenyl)pyrazole, and
4-chloro-1-(4-bromomethyl-2-bromophenyl)pyrazole.

(d) 15 g of 4-chloro-1-(4-bromomethyl-3-chlorophenyl)pyrazole are added to 2.8 g of sodium cyanide in 67 ml of dimethylsulfoxide and stirred for 6.5 hours at room temperature. 300 ml of water are added dropwise and 12.3 g of 2-chloro-4-(4-chloropyrazol-1-yl)phenylacetonitrile are thus obtained. Chromatographing the latter with a mixture of cyclohexane/ethanol/ethyl acetate on silica gel, yields a product with a m.p. 139.5° to 140° C. (As by-product, 1,2-bis-[2-chloro-4-(4-chloropyrazol-1-yl)phenyl]propionic acid nitrile has formed; from this by-product the appropriate amide with m.p. 248° to 249.5° C. is obtained by saponification with concentrated sulfuric acid.)

Analogously, [from the corresponding 4-halo-1-(4-bromomethyl-halophenyl)pyrazoles and sodium cyanide]

2-chloro-4-(4-bromopyrazol-1-yl)phenylacetonitrile,
3-chloro-4-(4-chloropyrazol-1-yl)phenylacetonitrile,
3-bromo-4-(4-bromopyrazol-1-yl)phenylacetonitrile,
3-chloro-4-(4-bromopyrazol-1-yl)phenylacetonitril and
3-bromo-4-(4-chloropyrazol-1-yl)phenylacetonitril are obtained.

EXAMPLE 16

(a) 86.5 ml (0.5 mole) of methylmalonic acid diethyl ester are added dropwise with good stirring under nitrogen at room temperature to a suspension of 12 g (0.5 mole) of sodium hydride in 500 ml of dimethylformamide. After cessation of evolution of hydrogen, 113.5 g (0.5 mole) of 1,2,4-trichloro-5-nitrobenzene are added dropwise and subsequently stirred for a further 2 hours at room temperature. Pouring onto 1 kg of ice is effected, followed by extracting five times with (in each case) 200 ml of cyclohexane, washing of the organic phase with water, drying, and distilling off the solvent. (2,5-dichloro-4-nitrophenyl)methylmalonic acid diethyl ester is thus obtained. This is boiled under reflux for 5 days in 2 liters of 6 N hydrochloric acid. Subsequently, cooling to room temperature is effected, followed by extracting with chloroform, and extracting the organic phase with sodium hydroxide solution. The aqueous phase is acidified with hydrochloric acid, and extraction with chloroform is effected. The organic phase is dried and concentrated in a vacuum to yield 109 g (82.5% of theory) of 2-(2,5-dichloro-4-nitrophenyl)propionic acid (m.p. 143° C.).

(b) 23 g (87 mmoles) of 2-(2,5-dichloro-4-nitrophenyl)propionic acid are heated to 95° C. in 100 ml of glacial acetic acid and 30 ml of water, and 14 g (0.25 mole) of iron powder are added in portions. After the exothermic reaction subsides, heating (to 95° C.) is effected for a further hour. Pouring onto 500 g of ice is effected, followed by extracting twice with, in each case, 200 ml of diethyl ether, washing the organic phase with water, drying, and concentrating in a vacuum to obtain 16 g (78.6% of theory) of 2-(4-amino-2,5-dichlorophenyl)propionic acid (m.p. 140° to 141° C.).

Analogously, reduction with iron powder of each of 2-(3-chloro-4-nitrophenyl)propionic acid and 2,6-dichloro-3-nitrophenylacetic acid yields 2-(4-amino-3-chlorophenyl)propionic acid (m.p. 114° C.) and
3-amino-2,6-dichlorophenylacetic acid (m.p. 172° C.), respectively.

EXAMPLE 17

3.86 g (10 mmoles) of 2-(3-chloro-4-hydraziniumphenyl)propionic acid p-toluenesulfonate and 100 mg of p-toluenesulfonic acid are dissolved in 100 ml of absolute ethanol and left to stand for 12 hours at room temperature. Pouring onto ice water is effected, followed by extracting with benzene, washing of the organic phase with sodium hydrogen carbonate solution and water and concentrating in a vacuum. 2-(3-chloro-4-hydrazinophenyl)propionic acid ethyl ester remains as an oil in the residue. A solution of hydrogen chloride in ethanol and 2.2 g (10 mmoles) of 1,1,3,3-tetraethoxypropane are added to the oil, and stirring is effected for 6 hours at room temperature. Subsequently, concentration is effected, and the residue is distilled to obtain 2-[3-chloro-4-(pyrazol-1-yl)phenyl]propionic acid ethyl ester (b.p. 120°/10$^{-2}$ mm Hg).

EXAMPLE 18

3.87 g (0.01 mole) of 2-(3-chloro-4-hydraziniumphenyl)propionic acid p-toluenesulfonate and 0.56 g (0.01 mole) of acrylaldehyde are stirred in 70 ml of tetrahydrofuran for 12 hours at room temperature. Concentration is effected, and the residue is chromatographed with benzene/ethyl acetate (1:1) over a silica gel column to obtain 1.2 g (47.5% of theory) of 2-[3-chloro-4-(2-pyrazolin-1-yl)phenyl]propionic acid (m.p. 94° to 102° C.).

EXAMPLE 19

252 mg (1 mmole) of 2-[3-chloro-4-(2-pyrazolin-1-yl)phenyl]propionic acid are heated to the boil for 8 hours with 250 mg of active manganese dioxide and 1 g molecular sieve 4 Å*) in 10 ml of toluene. Filtration is effected, followed by extraction first with 1 N hydrochloric acid and then with 1 N sodium hydroxide. The aqueous alkaline extract is acidified and subsequently extracted with benzene; the resulting organic phase is dried to yield 2-[3-chloro-4-(pyrazol-1-yl)phenyl]propionic acid (m.p. 83° to 85° C.).
(*) (Merck Darmstadt)

EXAMPLE 20

375 mg (1 mmole) of 2-[3-chloro-4-(4-chloropyrazol-1-yl)phenyl]propionic acid benzyl ester are hydrogenolyzed in the presence of 50 mg of 10% palladium/activated charcoal at room temperature and at atmospheric pressure in a mixture of 100 ml of ethyl acetate and 10 ml of glacial acetic acid in a rotary hydrogenation apparatus until the theoretical amount of hydrogen has been absorbed. Filtration from the catalyst is effected, the filtrate is concentrated in a vacuum, and the residue is dissolved in a 1 N solution of sodium hydroxide. The resulting aqueous solution is extracted with benzene; acidification is effected with 1 N hydrochloric acid, followed by extraction again with benzene. The organic phase is dried and concentrated to yield 230 mg (80.7% of theory) of 2-[3-chloro-4-(4-chloropyrazol-1-yl)phenyl]propionic acid (m.p. 102° to 103° C.).

EXAMPLE 21

341 mg (1 mmole) of 2-[3-chloro-4-(4-chloropyrazol-1-yl)phenyl]propionic acid tert.-butylester are heated to the boil for 2 hours with 10 mg of p-toluenesulfonic acid in toluene. The reaction solution is washed with water, dried and concentrated to obtain 270 mg (94.7% of theory) of 2-[3-chloro-4-(4-chloropyrazol-1-yl)phenyl]propionic acid (m.p. 102° to 103° C.).

EXAMPLE 22

100 ml of thionyl chloride are added to 28.51 g (0.1 mole) of 2-[3-chloro-4-(4-chloropyrazol-1-yl)phenyl]propionic acid and heated to the boil for half an hour. The solution is concentrated in a vacuum, and 2-[3-chloro-4-(4-chloropyrazol-1-yl)phenyl]propionic acid chloride is thus obtained. 500 ml of absolute methanol are added; and, again, heating to the boil for half an hour and concentrating are effected, followed by taking up in benzene, washing with water and sodium hydrogen carbonate solution, drying of the organic solution and distilling to produce 26 g (86.9% of theory) of 2-[3-chloro-4-(4-chloropyrazol-1-yl)phenyl]propionic acid methyl ester (b.p. 126° to 127° C./$10^{-2}$ mm Hg).

Analogously, from 2-[3-chloro-4-(4-chloropyrazol-1-yl)phenyl]propionic acid there are obtained (via the acid chloride) by reaction with each of ethanol, n-propanol, n-butanol, tert.-butanol, menthol, benzyl alcohol and borneol,
2-[3-chloro-4-(4-chloropyrazol-1-yl)phenyl]propionic acid ethyl ester (b.p. 134° C./$3.10^{-2}$ mm Hg),
2-[3-chloro-4-(4-chloropyrazol-1-yl)phenyl]propionic acid n-propyl ester (b.p. 132° C./$10^{-2}$ mm Hg),
2-[3-chloro-4-(4-chloropyrazol-1-yl)phenyl]propionic acid n-butyl ester (b.p. 140° C./$10^{-2}$ mm Hg),
2-[3-chloro-4-(4-chloropyrazol-1-yl)phenyl]propionic acid tert.-butyl ester (b.p. 141° C./$10^{-2}$ mm Hg, m.p. 87° to 95° C.),
2-[3-chloro-4-(4-chloropyrazol-1-yl)pyenyl]propionic acid menthyl ester (b.p. 178° C./$10^{-2}$ mm Hg),
2-[3-chloro-4-(4-chloropyrazol-1-yl)phenyl]propionic acid benzyl ester (b.p. 184° C./$7.10^{-3}$ mm Hg) and
2-[3-chloro-4-(4-chloropyrazol-1-yl)phenyl]propionic acid bornyl ester (b.p. 187° C./$10^{-2}$ mm Hg), respectively.

EXAMPLE 23

14.25 g (50 mmoles) of 2-[3-chloro-4-(4-chloropyrazol-1-yl)phenyl]propionic acid, 150 ml of ethanol and 7 g of concentrated sulfuric acid are heated to the boil for 10 hours. Concentration is effected, followed by pouring onto ice water, extracting with diethyl ether, washing of the organic solution with sodium hydrogen carbonate solution, drying the organic solution and distilling it to obtain 12.4 g (83% of theory) of 2-[3-chloro-4-(4-chloropyrazol-1-yl)phenyl]propionic acid ethyl ester (b.p. 134° C./$3·10^{-2}$ mm Hg).

Analogously, [from
3-bromo-4-(pyrazol-1-yl)phenylacetic acid,
4-(4-chloropyrazol-1-yl)phenylacetic acid,
3-chloro-4-(pyrazol-1-yl)phenylacetic acid,
3-chloro-4-(4-bromopyrazol-1-yl)phenylacetic acid and
4-(pyrazol-1-yl)mandelic acid,
and ethanol]
3-bromo-4-(pyrazol-1-yl)phenylacetic acid ethyl ester (b.p. 126° C./$10^{-2}$ mm Hg),
4-(4-chloropyrazol-1-yl)phenylacetic acid ethyl ester (m.p. 91° to 92° C.),
3-chloro-4-(pyrazol-1-yl)phenylacetic acid ethyl ester (b.p. 120° C./$10^{-2}$ mm Hg),
3-chloro-4-(4-bromopyrazol-1-yl)phenylacetic acid ethyl ester (b.p. 127° C./$10^{-2}$ mm Hg) and
4-(pyrazol-1-yl)mandelic acid ethyl ester (m.p. 93° to 95° C.), respectively, are obtained.

EXAMPLE 24

2.85 g (10 mmoles) of 2-[3-chloro-4-(4-chloropyrazol-1-yl)phenyl]propionic acid are dissolved (on heating) in 10 ml of 1 N sodium hydrogen carbonate solution and extracted with diethyl ether; the aqueous phase is concentrated, the resulting residue is rubbed with chloroform and recrystallized from chloroform to yield 2.8 g (91.2% of theory) of sodium 2-[3-chloro-4-(4-chloropyrazol-1-yl)phenyl]propionate (m.p. 115° to 128° C.).

In the same manner, from
2-[2,5-dichloro-4-(pyrazol-1-yl)phenyl]propionic acid and from
2-(4-chloropyrazol-1-yl)phenylacetic acid sodium 2-[2,5-dichloro-4-(pyrazol-1-yl)phenyl]propionate (m.p. 132° to 137° C.) and
sodium 2-(4-chloropyrazol-1-yl)phenyl acetate (m.p. 245° to 247° C.), respectively, are obtained.

EXAMPLE 25

80 g of L-1-phenylethylammonium salt of racemic 2-[3-chloro-4-(4-chloropyrazol-1-yl)phenyl]propionic acid are recrystallized from 1 liter of isopropanol. This process is repeated ten times until 1.8 g of pure L-1-phenylethylammonium-(−)2-[3-chloro-4-(4-chloropyrazol-1-yl)phenyl]propionate are obtained. For the isolation of the free acid, this salt is suspended in chloroform, and extraction is effected with 10 ml of 1 N hydrochloric acid; the organic phase is washed with water and concentrated to obtain (−)-2-[3-chloro-4-(4-chloropyrazol-1-yl)phenyl]propionic acid (m.p. 110° to 111° C.; $[\alpha]_D^{25} = -31.5°$; c=0,1, CHCl$_3$).

Analogously, from the D-1-phenylethylammonium salt of racemic 2-[3-chloro-4-(4-chloropyrazol-1-yl)phenyl]propionic acid, there is obtained (+)-2-[3- chloro-4-(4-chloropyrazol-1-yl)phenyl]propionic acid (m.p. 110° to 111° C.; $[\alpha]_D^{25} = +31.5°$; c=0,1, CHCl$_3$), by recrystallization and adicification.

EXAMPLE 26

2 g (9.06 mmoles) of 3-chloro-4-(pyrazol-1-yl)acetophenone, 0.58 g (18 mmoles) of sulfur and 0.78 g (9 mmoles) of morpholine are heated to the boil for 6 hours; then 4 ml of ethanol are added, and cooling is effected. 3-chloro-4-(pyrazol-1-yl)phenylthioacetomorpholide separates out as an oil. Decantation is effected, 4 g of potassium hydroxide in 14 ml of ethanol are added, and heating (to the boil) is effected for 6 hours. The ethanol is distilled off, water is added to the resulting residue, and extraction with diethyl ether is effected. The aqueous phase is clarified with activated charcoal; acidification is effected with hydrochloric acid, followed by extraction with benzene. The organic phase is dried and then concentrated to yield 1.06 g (49.4% of theory) of 3-chloro-4-(pyrazol-1-yl)phenylacetic acid as an oil.

The starting compound is obtained in the following manner:

680 mg (10 mmoles) of pyrazole are dissolved in 10 ml of dimethylformamide, and 300 mg (12.5 mmoles) of sodium hydride are added in the cold. After cessation of gas evolution, 1.89 g (10 mmoles) of 3,4-dichloroacetophenone are added, and heating to 100° C. is effected for 12 hours. Subsequently, cooling is effected, followed by pouring onto water and extracting six times with cyclohexane. Concentration is effected, and the residue is chromatographed with benzene over a silica gel column to yield 1.08 g (49% of theory) of 3-chloro-4-(pyrazol-1-yl)acetophenone as an oil.

EXAMPLE 27

44.5 g (0.164 mole) of 4-acetamido-3-bromophenylacetic acid and 131 ml of 6 N hydrochloric acid are heated to 100° C. for 2 hours. The solution of 4-amino-3-bromophenylacetic acid (which is thus formed) is cooled to −6° C. in an ice-sodium chloride bath, and a solution of 11.7 g (0.17 mole) of sodium nitrite in 130 ml of water is added dropwise thereto at −6° C. Stirring is continued for a further hour at the same temperature, and the thus-prepared solution of the diazonium salt is poured slowly into a solution (which is cooled to −10° C.) of 100 g (0.443 mole) of tin(II) chloride dihydrate in 100 ml of concentrated hydrochloric acid to form 3-bromo-4-hydraziniumphenylacetic acid chloride. Dilution of the latter with 300 ml of water is effected, and 36 ml (0.163 mole) of 1,1,3,3-tetraethoxypropane are added dropwise thereto; stirring is then effected for 4 hours at room temperature. The resulting reaction mixture is rendered alkaline with 35% strength solution of sodium hydroxide and is heated to 100° C. for one hour in order to hydrolyze 3-bromo-4-(pyrazol-1-yl)phenylacetic acid ethyl ester, which is formed simultaneously along with the corresponding free acid. The produced ethanol is distilled off, and clarification is effected with activated charcoal. This is followed by acidification with hydrochloric acid and extraction with chloroform. The organic phase is dried. Concentration to dryness is effected in a vacuum, and the residue is recrystallized from benzene to obtain 38.5 g (83.5% of theory) of 3-bromo-4-(pyrazol-1-yl)phenylacetic acid (m.p. 100° to 101° C.).

The starting compounds are obtained in the following manner:

(a) 150 g (0.83 mole) of 4-nitrophenylacetic acid are heated to 95° C. in 1.5 liters of glacial acetic acid. With vigorous stirring, 160 g (2.86 moles) of iron powder are added in portions in such a manner that the internal temperature does not rise above 105° C. Towards the end of the reaction, the reaction mixture clears up. 200 ml of acetic anhydride are added, and stirring is afterwards continued for a further 30 minutes at 100° C. Cooling to room temperature is allowed to take place; this is followed by suction filtration from formed iron salts, concentration to half the volume, and dilution with 1.5 liters of water. Extraction is effected three times with, in each case, one liter of ethyl acetate. This is followed by washing the organic phase with water and then concentrating it to dryness to obtain 133 g (83.1% of theory) of 4-acetamidophenylacetic acid (m.p. 168° to 170° C.).

(b) 102.2 g (0.64 mole) of bromine are added dropwise at room temperature, with stirring, to a suspension of 100 g (0.52 mole) of 4-acetamidophenylacetic acid in 1 liter of glacial acetic acid; during this dropwise addition, a solution forms intermittently. Subsequently, heating to 60° C. is effected for 12 hours, followed by cooling to room temperature, diluting with 2 liters of water and extracting three times with diethyl ether. The organic phase is washed with sodium hydrogen sulfite solution and water, dried and concentrated to dryness. The residue is recrystallized from acetonitrile to yield 78 g (55.3% of theory) of 4-acetamido-3-bromophenylacetic acid (m.p. 157° to 159° C.).

Analogously, [from 4-acetamidophenylacetic acid and one and two equivalents, respectively, of chlorine] 4-acetamido-3-chlorophenylacetic acid (m.p. 157° to 158° C.) and 4-acetamido-3,5-dichlorophenylacetic acid (m.p. 209° to 211° C.) are obtained.

(c) 30.5 g (0.112 mole) of 4-acetamido-3-bromophenylacetic acid are heated to 100° C. in 100 ml of 6 N hydrochloric acid until a clear solution forms, and the mixture is subsequently kept at 110° C. for one hour. Cooling is effected, followed by rendering alkaline with a solution of sodium hydroxide and acidifying with glacial acetic acid. The thus-formed flocculent precipitate is suction filtered, washed with water and dried to obtain 23.5 g (91.4% of theory) of 4-amino-3-bromophenylacetic acid (m.p. 139° to 140° C.).

Analogously, acid hydrolysis of
4-acetamido-3-chlorophenylacetic acid and of
4-acetamido-3,5-dichlorophenylacetic acid, yields
4-amino-3-chlorophenylacetic acid (m.p. 132° C.) and
4-amino-3,5-dichlorophenylacetic acid (m.p. 168° to 170° C.).

EXAMPLE 28

To a solution of 3.13 g (10 mmoles) of 2-[3-chloro-4-(4-chloropyrazol-1-yl)phenyl]propionic acid ethyl ester in 20 ml of dimethyl formamide there are added dropwise, at room temperature, 15 ml of hydrazine hydrate. Stirring is continued for a further 2 hours at room temperature, followed by pouring on to ice, extraction with methylene chloride, drying of the organic phase and concentration. 2-[3-chloro-4-(4-chloropyrazol-1-yl)phenyl]propionic hydrazide is obtained.

Dried hydrogen chloride is introduced for 30 minutes at 25° to 30° C. and 15 minutes at 0° C. into a solution of 280 mg (1 mmole) of 2-[3-chloro-4-chloropyrazol-1- yl)phenyl]propionic acid hydrazide in 200 ml of dry nitromethane; the hydrochloride precipitates. Dry chlorine is then introduced for 10 minutes with cooling at 0° to 3° C. The mixture is left to stand for 1 hour at 0° C., concentrated in a vacuum and distilled. 2-[3-chloro-4-(4-chloropyrazol-1-yl)phenyl]propionyl chloride (b.p. 160° C./2.10$^{-2}$ mm Hg) is obtained.

In analogous manner, there are obtained from the appropriate starting compounds, through reaction with hydrazine hydrate and chlorination of the hydrazides, 2-[3-chloro-4-(4-bromopyrazol-1-yl)phenyl]propionyl chloride,
2-[3-bromo-4-(pyrazol-1-yl)phenyl]propionyl chloride and
3-chloro-4-(4-chloropyrazol-1-yl)phenylacetyl chloride, respectively.

EXAMPLE 29

2.65 g (10 mmoles) of 2-[3-chloro-4-(4-aminopyrazol-1-yl)phenyl]propionic acid are dissolved in 10 ml of 25% strength hydrochloric acid, the solution is cooled to −3° C., and 1.04 g (15 mmoles) of sodium nitrite (dissolved in 5 ml of water) are added. After 10 minutes the reaction mixture is stirred into a solution of 2 g (20 mmoles) of copper(I) chloride. Heating to 100° C. ist then effected for 1 hour, followed by cooling, extraction with chloroform and purification through chromatography on silica gel (benzene/cyclohexane/glacial acetic acid 2:1:1). 2-[3-chloro-4-(4-chloropyrazol-1-yl)phenyl]propionic acid, m.p. 102°–103° C., is obtained.

Analogously, from the same starting compound with hydrobromic acid and copper(I) bromide there is obtained 2-[3-chloro-4-(4-bromopyrazol-1-yl)phenyl]propionic acid (m.p. 116°–117° C.).

The starting compound is obtained in the following manner: 22.8 g (59 mmoles) of 2-(3-chloro-4-hydraziniumphenyl)propionic acid p-toluenesulphonate and 9.8 g (64 mmoles) of sodium nitromalondialdehyde monohydrate are heated under reflux for 30 minutes in 180 ml of 80% strength ethanol. Concentration is then effected, followed by taking up with sodium bicarbonate and extraction with ether. The aqueous solution is acidified and extracted with ether. Through concentration of the ethereal phase there is obtained, after recrystallisation from ethanol, 2-[3-chloro-4-(4-nitropyrazol-1-yl)phenyl]propionic acid (m.p. 173°–173.5° C.). 5 g (16.9 mmoles) of 2-[3-chloro-4-(4-nitropyrazol-1-yl)phenyl]propionic acid are dissolved in 30 ml of glacial acetic acid, heated to 80° C.; portionwise, 3.8 g of iron powder and then 7 ml of water are added. After one hour, pouring on to ice is effected, followed by extraction with ether. The ether phase is dried, clarified with Tonsil, and concentrated. 2-[3-chloro-4-(4-aminopyrazol-1-yl)phenyl]propionic acid is obtained as oil [$R_F$=0.25 (silica gel; CHCl$_3$/ethanol 4:1)].

EXAMPLE 30

3 g (10 mmoles) of 2-[3-chloro-4-(4-chloropyrazol-1-yl)phenyl]propionyl chloride are stirred into 30 ml of concentrated aqueous ammonia solution. Stirring is continued for a further half hour at room temperature; adjustment to pH 12 is effected with sodium hydroxide solution, followed by extraction with ether, drying of the ethereal phase and concentration. 2-[3-chloro-4-(4-chloropyrazol-1-yl)phenyl]propionamide (m.p. 131°–132° C.) is obtained.

Analogously, there are obtained

N-methyl-2-[3-chloro-4-(4-chloropyrazol-1-yl)phenyl]propionamide,
N-ethyl-2-[3-chloro-4-(4-chloropyrazol-1-yl)phenyl]propionamide,
N-n-propyl-2-[3-chloro-4-(4-chloropyrazol-1-yl)phenyl]propionamide,
N,N-diethyl-2-[3-chloro-4-(4-chloropyrazol-1-yl)phenyl]propionamide,
N-benzyl-2-[3-chloro-4-(4-chloropyrazol-1-yl)phenyl]propionamide through reaction of 2-[3-chloro-4-(4-chloropyrazol-1-yl)phenyl]propionyl chloride with methyl amine, ethyl amine, propyl amine, diethyl amine, benzyl amine.

Analogously, from 2-[3-chloro-4-(4-bromopyrazol-1-yl)phenyl]propionyl chloride and methyl amine, diethyl amine or benzyl amine there are obtained
N-methyl-2-[3-chloro-4-(4-bromopyrazol-1-yl)phenyl]propionamide,
N,N-diethyl-2-[3-chloro-4-(4-bromopyrazol-1-yl)phenyl]propionamide or
N-benzyl-2-[3-chloro-4-(4-bromopyrazol-1-yl)phenyl]propionamide.

EXAMPLE 31

2.79 g (0.01 mole) of 2-[3-chloro-4-(pyrazol-1-yl)phenyl]propionic acid ethyl ester are dissolved in 30 ml of methylene chloride, and 700 mg of chlorine (dissolved in 5 ml of methylene chloride) are added. Stirring is effected for 12 hours at room temperature, followed by washing of the reaction solution with sodium carbonate solution and water, drying, concentration and distillation. 2-[3-chloro-4-(4-chloropyrazol-1-yl)phenyl]propionic acid ethyl ester is obtained.

Analogously, through reaction with bromine, 2-[3-chloro-4-(4-bromopyrazol-1-yl)phenyl]propionic acid ethyl ester is obtained.

EXAMPLE 32

266 mg (1 mmole) of 2-[3-chloro-4-(4-chloropyrazol-1-yl)phenyl]propionitrile and 2 ml of 25% strength hydrochloric acid are boiled under reflux for 6 hours. The mixture is rendered alkaline with concentrated sodium hydroxide solution, extracted with ether, clarified with activated charcoal, adjusted to pH 3 with mineral acid and again extracted with ether. The ethereal extract is dried and concentrated. 259 mg (91%) of 2-[3-chloro-4-(4-chloropyrazol-1-yl)phenyl]propionic acid are obtained. m.p. 102°–103° C.

Analogously, there are obtained from the appropriate nitriles:
3-chloro-4-(4-chloropyrazol-1-yl)phenylacetic acid (m.p. 132°–133° C.),
2-[3-chloro-4-(4-bromopyrazol-1-yl)phenyl]propionic acid (m.p. 116°–117° C.),
2-[3-bromo-4-(4-chloropyrazol-1-yl)phenyl]propionic acid (m.p. 124° C.),
2-[3-bromo-4-(4-bromopyrazol-1-yl)phenyl]propionic acid (m.p. 115°–116° C.),
2-[2-chloro-4-(4-bromopyrazol-1-yl)phenyl]propionic acid.

In analogous manner, from
N,N-dimethyl-2-[3-chloro-4-(4-chloropyrazol-1-yl)phenyl]propionamide, 2-[3-chloro-4-(4-chloropyrazol-1-yl)phenyl]propionamide or (L)-N-{2-[3-chloro-4-(4-chloropyrazol-1-yl)phenyl]propionyl}serine there is obtained, through acid hydrolysis, 2-[3-chloro-4-(4-chloropyrazol-1-yl)phenyl]propionic acid (m.p. 102°–103° C.) and from 3-chloro-4-(4-chloropyrazol-1-yl)phenylacetamide or N,N-dimethyl-3-chloro-4-(4-chloropyrazol-1-yl)phenylacetamide there is obtained 3-chloro-4-(4-chloropyrazol-1-yl)phenylacetic acid (m.p. 132°–133° C.).

EXAMPLE 33

2.7 g (10 mmoles) of 2-[3-chloro-4-(chloropyrazol-1-yl)phenyl]propionitrile are stirred for 12 hours at room temperature in 10 ml of concentrated sulphuric acid. The mixture is poured on to ice water, adjusted to pH 10 with sodium hydroxide solution and suction filtered. 2-[3-chloro-4-(4-chloropyrazol-1-yl)phenyl]propionamide (m.p. 131°–132° C.) is obtained.

Analogously, there are obtained from the appropriate nitriles
3-chloro-4-(4-chloropyrazol-1-yl)phenylacetamide (m.p. 130°–133° C.),
2-[3-chloro-4-(4-bromopyrazol-1-yl)phenyl]propionamide,
3-chloro-4-(4-bromopyrazol-1-yl)phenylacetamide,
3-bromo-4-(4-chloropyrazol-1-yl)phenylacetamide,
2-chloro-4-(4-bromopyrazol-1-yl)phenylacetamide.

EXAMPLE 34

31.3 g (0.1 mole) of 2-[3-chloro-4-(4-chloropyrazol-1-yl)phenyl]propionic acid ethyl ester are heated to 130° C. for 3 hours in a glass autoclave with 70 ml of concentrated aqueous ammonia and 30 ml of ethanol. After cooling, 100 ml of water and 20 ml of saturated sodium carbonate solution are added. Extraction is effected with benzene, the benzene phase is washed with water and dried and the solvent is evaporated off. After recrystallisation from ethanol, 24.47 g (86%) of 2-[3-chloro-4-(4-chloropyrazol-1-yl)phenyl]propionamide (m.p. 131°–132° C.) are obtained.

Analogously, there are obtained through reaction of aqueous ammonia with the appropriate ethyl esters:
3-chloro-4-(4-chloropyrazol-1-yl)phenylacetamide (m.p. 130°–133° C.),
2-[3-chloro-4-(4-bromopyrazol-1-yl)phenyl]propionamide,
3-chloro-4-(4-bromopyrazol-1-yl)phenylacetamide.
Analogously,
N,N-dimethyl-2-[3-chloro-4-(4-chloropyrazol-1-yl)phenyl]propionamide or
N,N-dimethyl-3-chloro-4-(4-chloropyrazol-1-yl)phenylacetamide is obtained through reaction of dimethyl amine with 2-[3-chloro-4-(4-chloropyrazol-1-yl)phenyl]propionic acid ethyl ester or 3-chloro-4-(4-chloropyrazol-1-yl)phenylacetic acid ethyl ester.

EXAMPLE 35

1.75 g (7 mmoles) of 3-chloro-4-(4-chloropyrazol-1-yl)phenylacetonitrile (dissolved in 2 ml of diethyl ether) are added dropwise, under nitrogen, to a freshly prepared solution of 273 mg (7 mmoles) of sodium amide (from 161 mg of sodium) in 10 ml of liquid ammonia. After 20 minutes, 10 ml of diethyl ether are added and the solution is warmed to room temperature; the ammonia is completely distilled off and 99.4 mg (7 mmoles) of methyl iodide are added to the ethereal solution. The ethereal solution is washed with water, dried and concentrated. Through distillation of the residue, 1.17 g (63%) of 2-[3-chloro-4-(4-chloropyrazol-1-yl)phenyl]propionitrile (b.p. 107°–109° C./$10^{-2}$ mm Hg) are obtained.

Analogously,
2-[3-chloro-4-(4-bromopyrazol-1-yl) phenyl] propionitrile is obtained from
3-chloro-4-(4-bromopyrazol-1-yl) phenylacetonitrile.

EXAMPLE 36

2.84 g (0.01 mmole) of 2-[3-chloro-4-(4-chloropyrazol-1-yl) phenyl] propionamide and 1 g (7 mmoles) of phosphorus oxy chloride are heated to 100° C. for one hour. The reaction mixture is cooled, washed with sodium carbonate solution and water, concentrated and distilled. 1.99 g (75%) of 2-[3-chloro-4-(4-chloropyrazol-1-yl) phenyl] propionitrile (b.p. 107°–109° C./$10^{-2}$ mm Hg) are obtained.

In analogous manner,
3-chloro-4-(4-chloropyrazol-1-yl) phenylacetonitrile (b.p. 104° C./$10^{-2}$ mm Hg) is obtained from
3-chloro-4-(4-chloropyrazol-1-yl) phenylacetamide.
Analogously,
2-[3-chloro-4-(4-bromopyrazol-1-yl) phenyl] propionitrile,
2-[3-bromo-4-(4-chloropyrazol-1-yl) phenyl] propionitrile,
2-[3-bromo-4-(4-bromopyrazol-1-yl) phenyl] propionitrile,
2-[2-chloro-4-(4-bromopyrazol-1-yl) phenyl] propionitrile
are obtained through reaction of the appropriate acid amides with phosphorus oxychloride.

EXAMPLE 37

2.11 g (8.7 mmoles) of 2-(3-chloro-4-hydrazinophenyl)propionic acid ethyl ester and 1.91 g of tetraethoxypropane are dissolved in 2 ml of absolute ethanol. The solution is saturated with hydrochloric acid gas and left to stand for half an hour. The solvent is evaporated off; the residue is distilled. 2 g (83%) of 2-[3-chloro-4-(pyrazol-1-yl) phenyl] propionic acid ethyl ester (b.p. 120° C./$10^{-2}$ mm Hg) are obtained.

Analogously,
3-chloro-4-(pyrazol-1-yl) phenylacetic acid ethyl ester (b.p. 120° C./$10^{-2}$ mm Hg),
4-(pyrazol-1-yl) phenylacetic acid ethyl ester (b.p. 112° C./$10^{-2}$ mm Hg),
3-bromo-4-(pyrazol-1-yl) phenylacetic acid ethyl ester (b.p. 126° C./$10^{-2}$ mm Hg),
2-[4-(pyrazol-1-yl) phenyl] propionic acid ethyl ester (b.p. 118° C./$10^{-2}$ mm Hg) are obtained through reaction of
3-chloro-4-hydrazinophenylacetic acid ethyl ester,
4-hydrazinophenylacetic acid ethyl ester,
3-bromo-4-hydrazinophenylacetic acid ethyl ester or
2-(4-hydrazinophenyl) propionic acid ethyl ester with tetraethoxypropane.

EXAMPLE 38

3.68 g (0.01 mole) of 2-(3-chloro-4-hydraziniumphenyl)propionic acid p-toluenesulphonate are dissolved in 20 ml of absolute ethanol, which is saturated with hydrogen chloride, and the solution is left to stand at room temperature for 24 hours. After the ethanol has been distilled off, the residue is taken up with benzene; the solution is washed with sodium carbonate solution, dried and concentrated. 2.11 g (87%) of 2-(3-chloro-4-hydrazinophenyl)propionic acid ethyl ester are obtained as oil, $R_F=0.37$. The $R_F$ value was determined by thin-layer chromatography on silica gel thin-layer chromatography plates F 1500 LS 254 (Schleicher and Schull) with chloroform as solvent.

In analogous manner, there are obtained from the appropriate acids and ethanol:
3-chloro-4-hydrazinophenylacetic acid ethyl ester,
4-hydrazinophenylacetic acid ethyl ester,
2-(4-hydrazinophenyl) propionic acid ethyl ester,
3-bromo-4-hydrazinophenylacetic acid ethyl ester.

EXAMPLE 39

340 mg of red phosphorus and 110 mg of iodine are added to 10 ml of glacial acetic acid. After 15 minutes, 2.8 g (0.01 mole) of 4-(4-chloropyrazol-1-yl) mandelic acid are added; heating under reflux is effected for 4 hours, followed by cooling, filtration, pouring on to a sodium sulphite solution and extraction with ether. The ethereal solution is dried and concentrated. 4-(4-chloropyrazol-1-yl) phenylacetic acid (m.p. 176°–178° C.) is obtained.

EXAMPLE 40

To 2.51 g (10 mmoles) of 4-(4-chloropyrazol-1-yl) phenylglyoxylic acid in 20 ml of 1,2-dimethoxyethane there are added 1.5 g (30 mmoles) of hydrazine hydrate and, after 15 minutes, 1.34 g of potassium hydroxide. Heating to 150° C. is effected for one hour, followed by pouring on to ice water, extraction with diethyl ether, acidification of the aqueous phase, extraction again with ether, concentration of the ethereal phase; 4-(4-chloropyrazol-1-yl) phenylacetic acid is obtained as oil.

The starting compound is obtained in the following manner: 2.46 g (10 mmoles) of 4-(pyrazol-1-yl) mandelic acid ethyl ester and 10 ml of thionyl chloride are heated to 40° C. for 10 minutes, the excess thionyl chloride is distilled off. α-chloro-4-(pyrazol-1-yl) phenylacetic acid ethyl ester (oil) is obtained.

2.65 g of α-chloro-4-(pyrazol-1-yl) phenylacetic acid ethyl ester are dissolved in 50 ml of carbon tetrachloride, and 2 ml of water are added. Chlorine is introduced for 30 minutes and the reaction mixture is washed with sodium carbonate solution; concentration is effected, followed by purification through column chromatography on silica gel. (cyclohexane/diethyl ether 4:1). 4-(4-chloropyrazol-1-yl) phenylglyoxylic acid ethyl ester is obtained which, through saponification analogously to Example 10 is converted into 4-(4-chloropyrazol-1-yl) phenylglyoxylic acid.

EXAMPLE 41

3.83 g (10 mmoles) of methyl-[3-chloro-4-(4-chloropyrazol-1-yl) phenyl] malonic acid diethyl ester, 1.4 g of potassium hydroxide, 5 ml of water and 15 ml of n-butanol are heated to the boil for 3 hours, with stirring. The solvent is evaporated off, the residue is dissolved in water, the aqueous solution is extracted with ether, acidification is effected with hydrochloric acid and the precipitate is filtered off. 2-[3-chloro-4-(4-chloropyrazol-1-yl) phenyl] propionic acid is obtained; m.p. 102°–103° C.

In analogous manner,
2-[3-chloro-4-(4-bromopyrazol-1-yl) phenyl] propionic acid (m.p. 116°–117° C.) and
2-[4-(4-bromopyrazol-1-yl) phenyl] propionic acid (m.p. 154°–155° C.) are obtained from
methyl-[3-chloro-4-(4-bromopyrazol-1-yl) phenyl] malonic acid diethyl ester and
methyl-[4-(4-bromopyrazol-1-yl) phenyl] malonic acid diethyl ester, respectively,
through reaction with potassium hydroxide and working up.

The malonic ester derivative required as starting compound is prepared as follows:

(a) 29.9 g (0.1 mole) of 3-chloro-4-(4-chloropyrazol-1-yl)phenylacetic acid ethyl ester and 130 ml of diethyl carbonate are heated to 80° C.; a sodium ethanolate solution (prepared from 2.4 g of sodium and 100 ml of ethanol) is added and the ethanol is distilled off. The bath temperature is increased to 230° C. and, thereafter, 70 ml of diethyl carbonate are once more added which subsequently is slowly distilled off. The residue is neutralised with ice-cold 2 N acetic and extracted with diethyl ether. The ethereal phase is washed with sodium carbonate, dried and concentrated.

3-chloro-[4-chloropyrazol-1-yl) phenyl]malonic acid diethyl ester is obtained.

Analogously, there is obtained from the appropriate pyrazolylphenylacetic acid esters and diethyl carbonate 3-chloro-[4-(4-bromopyrazol-1-yl) phenyl]malonic acid diethyl ester or [4-(4-bromopyrazol-1-yl) phenyl]malonic acid diethyl ester.

(b) 7.38 g (20 mmoles) of 3-chloro-4-(4-chloropyrazol-1-yl)phenylmalonic acid diethyl ester are dissolved in 20 ml of absolute ethanol; a solution of sodium ethanolate in ethanol (consisting of 470 mg of sodium in 20 ml of ethanol) is added; stirring is effected at 40° C. for half an hour and 2.84 g (20 mmoles) of methyl iodide are added. Boiling under reflux is effected for 4 hours; again, 2.84 g of methyl iodide are added, followed by heating for a further 2 hours, concentration, and taking up with diethyl ether. The ethereal phase is washed with sodium hydrogen sulphite solution and water, dried and concentrated. Methyl-[3-chloro-4-(4-chloropyrazol-1-yl) phenyl] malonic acid diethyl ester is obtained.

Analogously, there is obtained from the appropriate pyrazolylphenylmalonic acid esters and methyl iodide methyl-[3-chloro-4-(4-bromopyrazol-1-yl) phenyl] malonic acid diethyl ester or methyl-[4-(4-bromopyrazol-1-yl) phenyl] malonic acid diethyl ester.

EXAMPLE 42

852 mg (3 mmoles) of 2-[3-chloro-4-(4-chloropyrazol-1-yl)phenyl] propionic acid are dissolved in 30 ml of 1,2-dimethoxyethane, and 0.35 g of triethyl amine are added. The solution is cooled to −10° to −15° C., 0.4 g of chloroformic acid isobutyl ester is added and stirring is effected for 30 minutes at −10° C. Subsequently, a solution of 0.3 g of (L)-serine in 20 ml of dimethyl formamide and 15 ml of water with addition of 0.35 g of triethyl amine is added dropwise to the above solution, while keeping to a temperature below −10° C., and stirring is continued for a further 30 minutes; the mixture is then left to stand over night at −15° C.

After the solvent has been evaporated in a vacuum, the residue is taken up in methylene chloride and extracted twice with 2 N HCl, then washed with water. The organic phase is concentrated. 530 mg [48% of theory] of (L)-N-{2-[3-chloro-4-(4-chloropyrazol-1-yl) phenyl] ropionyl} serine are obtained as glassy residue.

EXAMPLE 43

10,000 tablets with an active substance content of 50 mg are prepared from the following constituents: 500 g 2-[3-chloro-4-(4-chloropyrazol-1-yl)phenyl]propionic acid

| | |
|---|---|
| 700 g | maize starch |
| 450 g | lactose |
| 30 g | amorphous silicic acid |
| 40 g | sodium lauryl sulfate |
| 50 g | polyvinylpyrrolidone |
| 160 g | pectin |
| 50 g | talc |
| 20 g | magnesium stearate |
| 2000 g | |

The active substance, the maize starch, the lactose, the amorphous silicic acid and the sodium lauryl sulfate are mixed and sieved. This mixture is moistened with a solution of the polyvinylpyrrolidone in 320 ml of ethanol and granulated through a seive with a mesh size of 1.25 mm. The granulate is dried at 40° C. and mixed with pectin, talc and magnesium stearate. This mixture is compressed into tablets of 200 mg each and with a diameter of 8 mm.

EXAMPLE 44

10,000 capsules with an active substance content of 50 mg are prepared from the following constitutents:

| | |
|---|---|
| 500 g | 2-[3-chloro-4-(4-chloropyrazol-1-yl)phenyl]propionic acid |
| 495 g | microcrystalline cellulose |
| 5 g | amorphous silicic acid |
| 1000 g | |

The active substance in finely-powdered form, the micro-crystalline cellulose and the uncompressed amorphous silicic acid are mixed well and filled into hard gelatin capsules, size 4.

EXAMPLE 45

10 kg of 2-[3-chloro-4-(4-chloropyrazol-1-yl)phenyl]-propionic acid, 4.5 kg of dextropropoxyphene hydrochloride and 5.3 kg of potato starch are sprayed in a fluidized-bed granulator with a solution of 0.5 kg of polyvinylpyrrolidone (average molecular weight of 25,000) in 5 liters of water. After drying to a relative moisture of from 50 to 60%, 1.8 kg of carboxymethylcellulose and 0.2 kg of magnesium stearate are added; the mixture is then homogenized and sieved. Thereafter, the resulting granulate is compressed into 100,000 tablets of 8 mm diameter with a break score.

EXAMPLE 46

2.393 kg of Suppocire ® (suppository mass on basis of hydrogenated palm oil) are heated to from 40° to 45° C. 0.106 kg of 2-[3-chloro-4-(4-chloropyrazol-1-yl)phenyl]propionic acid (as sodium salt) are stirred into the resulting melt.

The suppository composition is homogenized and subsequently poured into molds to produce 1,000 suppositories.

EXAMPLE 47

1.50 kg of Carbopol ® 934 (carboxypolymethylene) are suspended in 76.50 kg of water, with high-frequency stirrer rotation. The resulting mixture is left to stand for 1 hour before 1.00 kg of 3-chloro-4-(4-chloropyrazol-1-yl)phenylacetic acid, 0.30 kg of Cremophor ® EL (mixture obtained by reaction of castor oil with ethylene oxide) and 20 kg of propyleneglycol are added. About 0.40 kg of sodium hydroxide solution is added to the mixture, slowly and with stirring, until a pH of 8 is achieved. A batch of 100 kg of gel is thus prepared.

EXAMPLE 48

2.70 kg of Tylose ® C. 30 (sodium salt of cellulose-O-acetic acid) are added to 90 liters of water, with vigorous stirring; then 1.00 kg of 2-[3-chloro-4-(4-chloropyrazol-1-yl)phenyl]propionic acid, 0.11 kg of sodium cyclamate and 0.08 kg of sorbic acid are added, and the volume is made up to 100 liters with water. The mixture is put through a corundum disk mill, subsequently de-aerated and then filled into 5 ml fractions. 100 liters of suspension are thus prepared.

EXAMPLE 49

65 liters of distilled water are heated to 80° C., with $N_2$ gassing; then 4.152 kg of 2-[3-chloro-4-(4-chloropyrazol-1-yl)phenyl]propionic acid (as sodium salt) and 0.150 kg of prednisolone are added thereto. After solution is complete, cooling is effected to room temperature, 0.200 kg of sodium disulfite, 0.025 kg of cysteine hydrochloride and 26.00 kg of 1,2-propyleneglycol are added, and the volume is made up to 100 liters with distilled water. Stirring is thereafter effected until solution is complete. 100 liters of an injection solution are thus prepared.

EXAMPLE 50

The procedure of Example 49 is followed but, instead of 0.150 kg of prednisolone, 0.08 kg of dexamethasone is used to produce 100 liters of an injection solution.

In a manner analogous to that of Examples 43 to 50, corresponding pharmaceutical preparations for other 4-halogenpyrazol-1-yl-phenylacetic acids or phenylpropionic acids are prepared;
in lieu of the compounds,
2-[3-chloro-4-(4-chloropyrazol-1-yl)phenyl]propionic acid and
3-chloro-4-[4-chloropyrazol-1-yl]phenylacetic acid,
in each case there are used, in the equivalent amount,
2-[4-(4-chloropyrazol-1-yl)phenyl]propionic acid,
2-[4-(4-bromopyrazol-1-yl)phenyl]propionic acid,
3-chloro-4-[4-bromopyrazol-1-yl]phenylacetic acid or
2-[3-chloro-4-(4-bromopyrazol-1-yl)phenyl]propionic acid.

The invention and its advantages are readily understood from the preceding description and specific examples. Various changes may be made in the structure of the compounds and/or in the formulation of the compositions without departing from the spirit and scope of the invention or sacrificing its material advantages. The depicted compounds (both intermediates and physiologically-acceptable active ingredients prepared therefrom), medicament compositions and regimens for administration are merely illustrative of preferred embodiments of the invention.

What is claimed is:

1. A compound of the formula

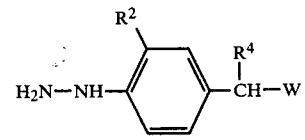

wherein
R² is a halo, $R^4$ is —H or lower alkyl,
W is —CN or —CO—Y and
Y is —OH, di(lower)alkylamino, lower alkoxy or benzyloxy.

2. A member selected from the group consisting of a compound according to claim 1:
wherein
$R^4$ is —H or —CH$_3$ and
W is —CO—OH,
and a salt thereof with a base.

3. A member according to claim 2 wherein $R^2$ is chloro or bromo.

4. A member according to claim 3 wherein $R^2$ is chloro.

5. A compound according to claim 1 wherein W is —CN.

6. A compound according to claim 1 wherein W is —CO—Y.

7. A compound according to claim 6 wherein Y is —OH.

8. A compound according to claim 6 wherein Y is di(lower)alkylamino.

9. A compound according to claim 6 wherein Y is lower alkoxy.

10. A compound according to claim 6 wherein Y is benzyloxy.

11. The compound according to claim 1 which is 2-(3-chloro-4-hydrazinophenyl)propionic acid.

12. The p-toluenesulfonate of the compound according to claim 11 which is 2-(3-chloro-4-hydrazinium-phenyl)propionic acid p-toluenesulfonate.

13. The compound according to claim 9 which is 2-(3-chloro-4-hydrazinophenyl)propionic acid ethyl ester.

* * * * *